(12) United States Patent
Dhiman et al.

(10) Patent No.: US 10,994,035 B2
(45) Date of Patent: May 4, 2021

(54) DISINFECTING SYSTEM WITH PERFORMANCE MONITORING

(71) Applicant: 3M INNOVATIVE PROPERTIES COMPANY, St. Paul, MN (US)

(72) Inventors: Rajeev Dhiman, Pleasanton, CA (US); Michael E. Griffin, Maplewood, MN (US); Robert E. Astle, Middlefield, CT (US); Michael N. Cormier, Burlington, CT (US)

(73) Assignee: 3M Innovative Properties Company, St. Paul, MN (US)

( * ) Notice: Subject to any disclaimer, the term of this patent is extended or adjusted under 35 U.S.C. 154(b) by 294 days.

(21) Appl. No.: 16/062,403

(22) PCT Filed: Dec. 19, 2016

(86) PCT No.: PCT/US2016/067442
§ 371 (c)(1),
(2) Date: Jun. 14, 2018

(87) PCT Pub. No.: WO2017/112568
PCT Pub. Date: Jun. 29, 2017

(65) Prior Publication Data
US 2018/0369435 A1    Dec. 27, 2018

Related U.S. Application Data

(60) Provisional application No. 62/270,861, filed on Dec. 22, 2015.

(51) Int. Cl.
*A61L 2/10* (2006.01)
*A61L 2/24* (2006.01)
(Continued)

(52) U.S. Cl.
CPC ...... *A61L 2/10* (2013.01); *A61L 2/24* (2013.01); *A61L 2/26* (2013.01); *A61L 2/28* (2013.01);
(Continued)

(58) Field of Classification Search
CPC ...... A61L 2/10; A61L 2/26; A61L 2/28; A61L 2/24; A61L 2202/14; G01J 1/44; G01J 1/429; G01J 0/228; G01J 2001/4247
See application file for complete search history.

(56) References Cited

U.S. PATENT DOCUMENTS

| 5,268,635 A | 12/1993 | Bortolini |
| 6,410,940 B1 | 6/2002 | Jiang |

(Continued)

FOREIGN PATENT DOCUMENTS

| CN | 103713673 A | 4/2014 |
| WO | WO 2006/012737 | 2/2006 |

(Continued)

OTHER PUBLICATIONS

Mims, "Sun photometer with light-emitting diodes as spectrally selective detectors", Applied Optics, Nov. 20, 1992, vol. 31, No. 33, pp. 6965-6967.

(Continued)

*Primary Examiner* — Regina M Yoo
(74) *Attorney, Agent, or Firm* — Scott A. Baum

(57) ABSTRACT

A system includes multiple devices configured to emit and detect germicidal radiation. Each of the multiple devices operates in emitting mode when connected to a drive source in a forward bias configuration and operates in detecting mode when disconnected from the drive source or when connected to the drive source in a reverse bias configuration. Cycling circuitry generates a sequence of control signals that control switching circuitry to change the connections of the devices to the drive source in a cycle in which one or more (Continued)

of the multiple devices are switched to detecting mode and senses radiation emitted by one or more of the multiple devices simultaneously operating in emitting mode. Each device operating in detecting mode generates a signal in response to the sensed radiation. Detection circuitry detects signals of the devices operating in detecting mode and generates a detection output in response to the detected signals.

23 Claims, 15 Drawing Sheets

(51) Int. Cl.
  *A61L 2/28* (2006.01)
  *G01J 1/44* (2006.01)
  *G01J 1/42* (2006.01)
  *G01J 1/02* (2006.01)
  *A61L 2/26* (2006.01)
(52) U.S. Cl.
  CPC ............ *G01J 1/0228* (2013.01); *G01J 1/429* (2013.01); *G01J 1/44* (2013.01); *A61L 2202/14* (2013.01); *G01J 2001/4247* (2013.01)

(56) References Cited

U.S. PATENT DOCUMENTS

| | | | |
|---|---|---|---|
| 6,825,620 B2 * | 11/2004 | Kuennen | H05B 41/36 315/224 |
| 7,008,795 B2 | 3/2006 | Yerazunis | |
| 7,072,587 B2 | 7/2006 | Dietz | |
| 7,170,606 B2 | 1/2007 | Yerazunis | |
| 7,329,998 B2 | 2/2008 | Jungwirth | |
| 7,960,699 B2 * | 6/2011 | Chang | G01J 1/32 250/338.4 |
| 8,203,124 B2 | 6/2012 | Havens | |
| 8,653,484 B2 | 2/2014 | Rudolph | |
| 9,150,434 B2 | 10/2015 | Basu | |
| 9,179,703 B2 | 11/2015 | Shur | |
| 2008/0075629 A1 | 3/2008 | Deal | |
| 2008/0197300 A1 * | 8/2008 | Kayser | G01J 1/02 250/504 R |
| 2010/0264835 A1 | 10/2010 | Bilenko | |
| 2012/0261595 A1 | 10/2012 | Inui | |
| 2014/0341777 A1 | 11/2014 | Deshays | |
| 2015/0353984 A1 * | 12/2015 | Pederson | C12Q 1/22 435/31 |

FOREIGN PATENT DOCUMENTS

WO    WO 2014-116065    7/2014
WO    WO 2018/048654    3/2018

OTHER PUBLICATIONS

Ozeki, "Half-duplex optical transmission link using an LED source-detector scheme", Optics Letters, Apr. 1978, Val. 2, No. 4, pp. 103-105.
International Search Report for PCT International Application No. PCT/US2016/067442, dated Apr. 7, 2017, 3 pages.

* cited by examiner

DISINFECTING SYSTEM WITH PERFORMANCE MONITORING

CROSS REFERENCE TO RELATED APPLICATIONS

This application is a national stage filing under 35 U.S.C. 371 of PCT/US2016/067442, filed Dec. 19, 2016, which claims the benefit of U.S. Provisional Patent Application No. 62/270,861 filed Dec. 22, 2015, the disclosures of which are incorporated by reference in their entirety herein.

TECHNICAL FIELD

This disclosure relates generally to radiation-based disinfecting systems.

BACKGROUND

Radiation-based disinfection systems use short wavelength photonic emission, e.g., emission in the ultraviolet (UV) range, to reduce microorganisms in fluids (e.g. drinking water) or on surfaces. UV radiation emitted by the source of a radiation-based disinfection system disrupts biological functions of microorganisms and retards or prevents their reproduction. Degradation or failure of the radiation source and/or loss of UV transmittance of the substance being disinfected can present a health risk. Therefore, the radiation intensity of the disinfection system may be monitored to detect changes that could compromise the disinfecting capability of the system.

SUMMARY

Some embodiments are directed to a system that includes multiple devices configured to operate in radiation emitting mode and radiation detecting mode. Each of the devices, when used in conjunction with appropriate circuitry, emits and detects radiation that is germicidal in wavelength and intensity. The system includes at least one drive source, wherein each of the multiple devices operates in emitting mode when connected to the drive source in a forward bias configuration and operates in detecting mode when disconnected from the drive source or when connected to the drive source in a reverse bias configuration. Switching circuitry is coupled to each of the devices and to the drive source. Cycling circuitry generates a sequence of control signals that control the switching circuitry to change the connections of the devices to the drive source in a cycle in which one or more of the multiple devices is switched to detecting mode and senses radiation emitted by one or more of the multiple devices simultaneously operating in emitting mode. Each device operating in detecting mode generates a signal in response to the sensed radiation. Detection circuitry detects signals of the devices operating in detecting mode and generates a detection output in response to the detected signals.

According to some embodiments, a method includes operating multiple devices capable of emitting and detecting radiation that is germicidal in wavelength and intensity in a cycle by generating a sequence of control signals that switch one or more of the multiple devices to detecting mode during the cycle. Each device of the multiple devices, when operating in detecting mode, senses radiation emitted by one or more of the multiple devices simultaneously operating in emitting mode and generates an electrical signal responsive to the sensed radiation. The electrical signals of the devices operating in detecting mode are detected and a detection output is generated in response to the detected electrical signals. The detection output indicates an intensity of the radiation sensed by the devices operating in detecting mode during the cycle.

Some embodiments involve a system that includes multiple devices configured to operate in emitting mode and detecting mode. Each of the devices, when used in conjunction with appropriate circuitry, emits and detects radiation that is germicidal in wavelength and intensity. The system includes at least one drive source, wherein each of the multiple devices are configured to operate in emitting mode when connected to the drive source in a forward bias configuration and to operate in detecting mode when disconnected from the drive source or when connected to the drive source in a reverse bias configuration. Switching circuitry is coupled to each of the devices and to the drive source. Cycling circuitry generates a sequence of control signals that control the switching circuitry to change the connections of the devices to the drive source in a cycle. During the cycle one or more of the multiple devices is switched to detecting mode and senses radiation emitted by one or more of the multiple devices simultaneously operating in emitting mode. Each device operating in detecting mode generates a signal in response to the sensed radiation. Detection circuitry detects the electrical signals of the devices operating in detecting mode and generates a detection output in response to the detected signals. Monitoring/control circuitry monitors the detection output for a low radiation intensity condition. The cycling circuitry and the monitoring/control circuitry can be implemented as a microprocessor executing programmed instructions.

BRIEF DESCRIPTION OF DRAWINGS

The figures are not necessarily to scale. Like numbers used in the figures refer to like components. However, it will be understood that the use of a number to refer to a component in a given figure is not intended to limit the component in another figure labeled with the same number.

DETAILED DESCRIPTION OF ILLUSTRATIVE EMBODIMENTS

Figure 1A:
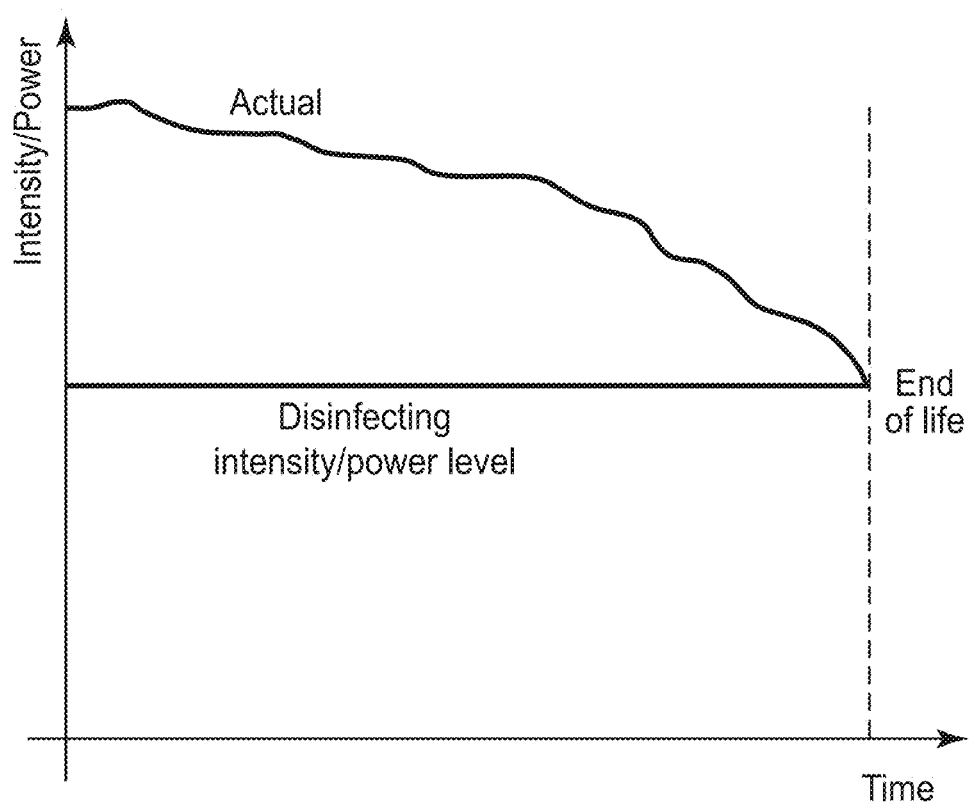
FIG. 1A is a graph of the radiation intensity of the disinfection system with respect to time under certain conditions.

A system includes multiple devices configured to operate in emitting mode and detecting mode. Each device may be configured to emit radiation that is germicidal in wavelength and intensity when the device is operated in emitting mode. Each device is configured to detect radiation of the same wavelengths as the radiation it emits. Switching circuitry is electrically coupled to each device and to at least one drive source. Cycling circuitry is configured to generate a sequence of control signals that control the switching circuitry to implement one or more cycles in which connections between the devices and a drive source are changed so that one or more of the multiple devices are switched to detecting mode during each cycle while one or more other devices are operated in emitting mode. For example, switching the devices to detecting mode according to the sequence during the cycle may involve switching the multiple devices to detecting mode one-by-one, two-by-two, or according to any other pattern. In some embodiments, each of the multiple devices is operated in detecting mode at least once during a cycle. In some embodiments, some, but not all, of the multiple devices operate in detecting mode during a cycle. In some embodiments, only one of the multiple devices operates in detecting mode at any particular period of time during the cycle. In other embodiments two or more of the multiple devices simultaneously operate in detecting mode during at least one period of time of the cycle.

Each device operating in detecting mode senses radiation that is emitted by at least one of the multiple devices that is simultaneously operating in emitting mode. Each device operating in detecting mode generates a signal in response to the sensed radiation.

The systems disclosed herein provide an average level of photonic emission for disinfection that is a high percentage of the maximum possible output if all devices were emitting. In many implementations, each device is in emission mode the majority of the time, with the period when switched in the detection mode being only a small fraction of the total time in operation. Further, the cycling of device switching leaves the majority of devices in emission mode while one, or a few devices are in the detection mode. The cycling provides a system in which the average level of UV emissions for disinfection is a high percentage of the maximum possible devices output if all were emitting, e.g., from about 60% to a significantly higher percentage, depending on cycling sequence. According to the disclosed approaches herein, the devices can be used for multiple purposes in the system. When the devices operate as emitters, they emit germicidal radiation; when the devices operate as detectors, they sense the emission of other devices that are operating as emitters. In some embodiments, the outputs of the devices operating as detectors are monitored for performance and/or the indication of a low emission condition which may compromise the capability of the system. In some embodiments, the outputs of the devices are used to control the operation of the devices in subsequent cycles when the devices are operated in emitting mode.

The performance monitoring aspects of the system can be used to enhance management of the radiation intensity of the devices over the life time of the system. For example, the power output of the emitting devices described herein typically decreases over their lifetime. This would require the system to be designed at the end-of-life power output, which implies that during the majority of the lifetime of the system, the UV intensity of some or all of the devices would be higher than that needed to achieve the desired level of disinfection, as illustrated by the graph of FIG. 1A. The performance monitoring aspects of the system can reduce the excess intensity by, for example, reducing the current input to the devices. Reducing excess intensity not only enhances energy efficiency, but also may increase device lifetime due to operation of the devices at lower input currents. Performance monitoring can also manage power during a temporary drop in the UV transmittance of the fluid. In such a scenario, the input current when the UV transmittance of the fluid is lower may be increased to provide increased UV intensity.

One cycling approach is to select and switch each device to detecting mode in a prescribed sequential pattern. This fixed pattern can be very effective for disinfection while verifying system and device operating behavior. The feedback from the UVLEDs in the detection mode may be used to generate information which can tell the controller to change the sequence, the repetition rate of the cycling, and/or to isolate/lock out certain devices or parts of the system. The ability for the cycling circuitry to adapt based on the provided feedback and/or other inputs provides for smart cycling.

Figure 1B:
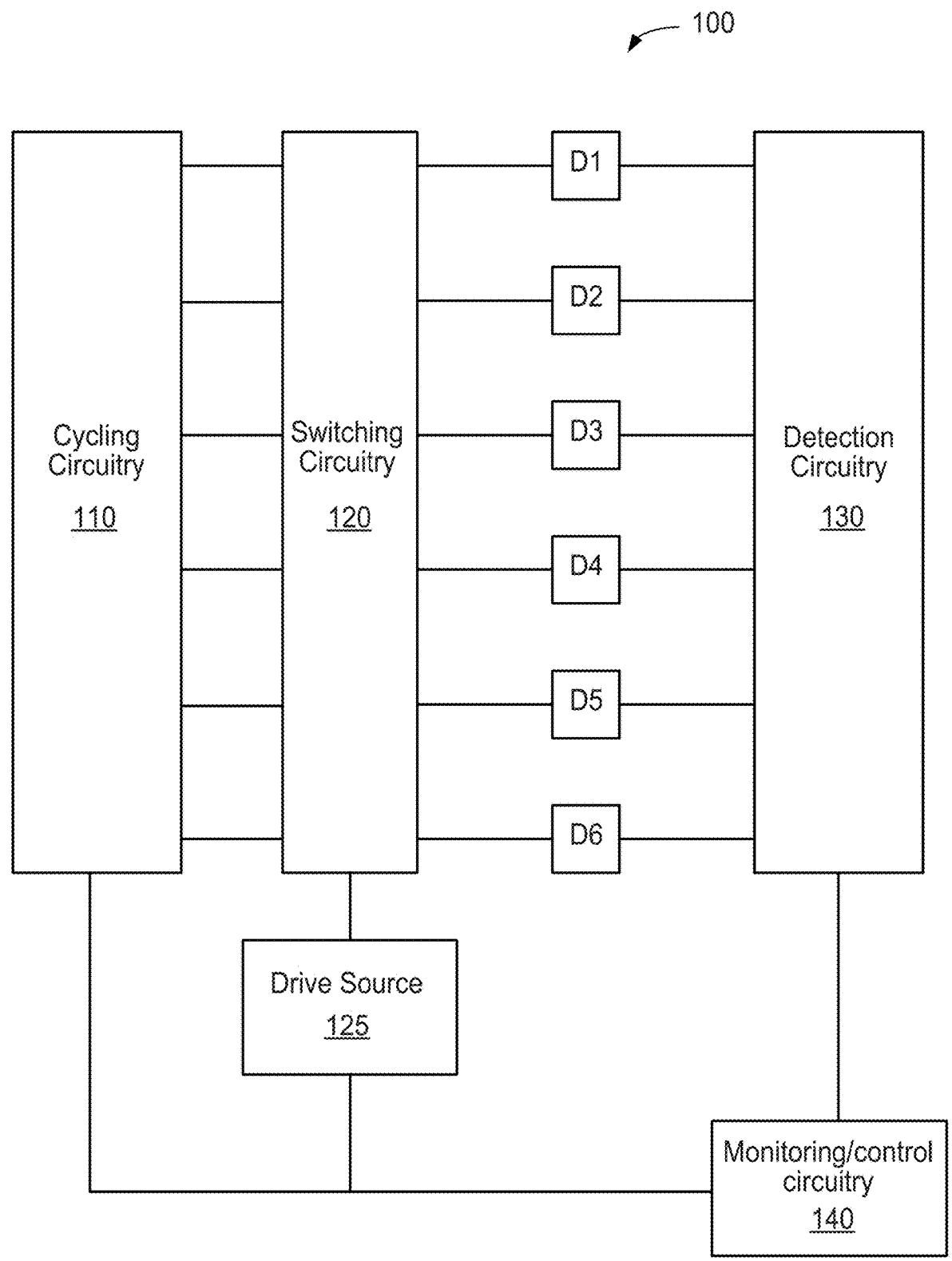
FIG. 1B is a block diagram of a system in accordance with some embodiments.

FIG. 1B is a block diagram of a system 100 in accordance with some embodiments. In this particular example, the system 100 includes six devices D1-D6. Each of the devices D1-D6 may comprise one or more UV light emitting diodes (UVLEDs) capable of emitting and detecting radiation that is germicidal in wavelength and intensity when used in conjunction with appropriate circuitry. In some implementations, the devices D1-D6 may be multi-chip UVLED packages, wherein one or more of the devices D1-D6 can include 2, 3, 4, or more UVLED chips housed in a single device package. The UVLED chips in the package can be interconnected, e.g. in series. It will be appreciated that more or fewer devices may be used depending on the application.

Devices D1-D6 are selectively coupled to a drive source 125 by switching circuitry 120. The operation of the devices D1-D6 is controlled by cycling circuitry 110 and switching circuitry 120. The cycling circuitry 110 is configured to generate a sequence of control signals that control the switching circuitry to implement a cycle during which connections between at least some of the devices and the drive source 125 are changed during a cycle. During portions of the cycle some of the devices D1-D6 are connected to the drive source in a way that causes the devices to operate in emitting mode while simultaneously other devices D1-D6 operate in detecting mode. The devices are switched to detecting mode during the cycle according to the sequence of control. For example, the sequence can involve switching the devices into detecting mode one-by-one, two-by-two or according to any other pattern while the other devices operate in emitting mode. For example, connecting UVLEDs to a forward bias source operates the UVLEDs in emitting mode and connecting the UVLEDs in reverse bias, or in bias-removed mode with appropriate circuitry operates the UVLEDs in detecting mode.

When operating as a detector, each device D1-D6 generates an electrical signal in response to radiation emitted by other devices that falls on the radiation sensitive surface of the device operating as a detector. For example, when device D1 operates as a detector, device D1 may sense radiation being emitted by one or more of devices D2-D6. The system 100 includes detection circuitry 130 coupled to detect the electrical signal generated by the devices. In some embodiments, the system 100 includes monitoring/control circuitry 140 configured to analyze the output of the detection circuitry 130. The monitoring/control circuitry 140 may monitor the output of the detection circuitry 130 for indication of a low emission due to catastrophic failure and/or gradual degradation of the devices D1-D6, for example.

The monitoring/control circuitry 140 can be configured to trigger an alarm if the detection circuitry output indicates a low radiation emission condition or other anomaly. In some embodiments, the monitoring/control circuitry 140 may be configured to generate a feedback signal based on the detection output of the detection circuitry 130. The feedback signal can control the drive source 125 to increase or decrease the drive signal, and thus increase or decrease the intensity of the radiation emitted by devices D1-D6. In some embodiments, the drive source 125 provides one drive signal that drives each of the devices operating in emitting mode collectively. In other embodiments the drive source 125 provides multiple drive signals such that each device D1-D6 can be operated with a different drive signal.

In some embodiments, the monitoring/control circuitry 140 can be configured to control the cycling circuitry 110. For example, based on the detection output, the monitoring/control circuitry may change various parameters of the cycle, e.g., the devices switched to detection mode during a cycle, the pattern of devices switched to detection mode, e.g., a one-by-one pattern, two-by-two pattern, etc., the detection time of each of the devices, cycle idle time, and/or other cycle parameters.

FIG. 1B illustrates devices D1 through D6 that can be cycled between emitting mode and detecting mode. It will be appreciated that such a system may additionally include other radiation emitting devices that are not switched and that operate continuously in emitting mode or detecting mode.

Figure 2A:
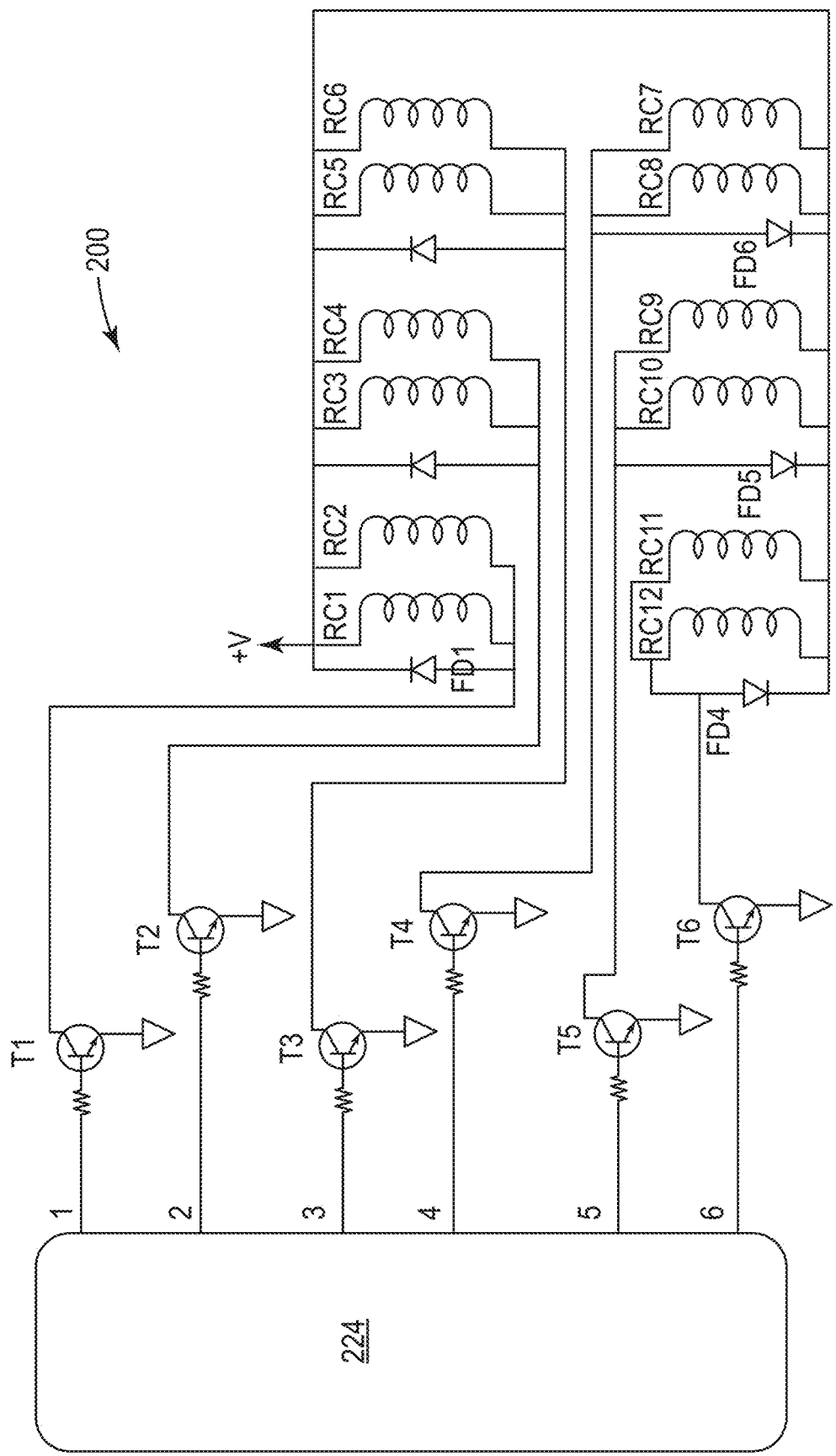
FIGS. 2A and 2B provide a circuit schematic of a system in accordance with some embodiments.
Figure 2B:
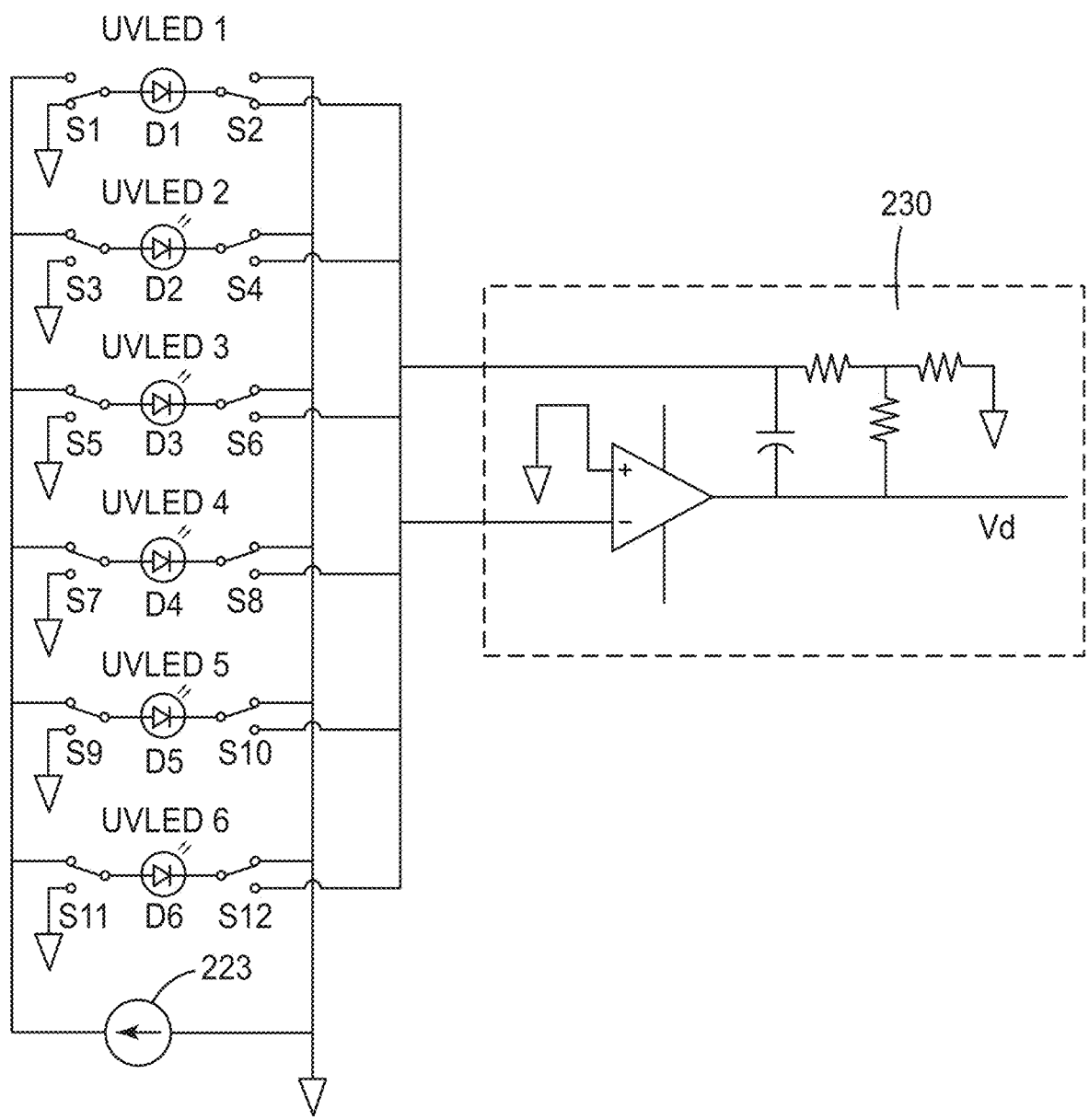

FIGS. 2A and 2B provide a circuit schematic of a disinfection system 200 in accordance with some embodiments. In this example, devices D1 through D6 are ultraviolet light emitting diodes (UVLEDs) configured to emit and detect ultraviolet radiation that is germicidal in wavelength and intensity. For example, in some disinfection applications, a useful wavelength range for the ultraviolet radiation is between 200 nm and 300 nm. When forward biased, each of the UVLEDs 1-6 operates as an emitter. When unbiased or reverse biased, each of the UVLEDs 1-6 operates as a detector, generating a current in response to radiation falling on the radiation sensitive surface of the UVLED 1-6.

Switching circuitry, comprising transistors T1-T6, inductors RC1-RC12 and switches S1-S12, is configured to selectively connect or disconnect the UVLEDs 1-6 to bias source 223. Cycling circuitry, comprising microprocessor 224, is configured to generate a sequence of control signals on outputs 1-6. The control signals cycle at least some of the UVLEDs 1-6 between emitting mode and detecting mode during a cycle according to the sequence of control signals. In FIG. 2B, device D1 is shown switched to detecting mode and devices D2-D6 are shown switched to emitting mode.

The bias source 223 is used to forward bias the UVLEDs 1-6. The switches S1-S12 are controlled by cycling circuitry 224 to selectively change the connections between the UVLEDs 1-6 and the bias source 223.

The system illustrated in FIGS. 2A and 2B shows UVLEDs 1-6 that can be selectively coupled to be driven by a single bias source 223, e.g., a constant current source. In this scenario, the electrical current provided by the bias source 223 is divided among the UVLEDs switched into emitting mode. These emitting UVLEDs are connected in parallel in this example. The current through each UVLED will be roughly the same when the same number of devices are in emission mode in this switching scheme, e.g., five emitting devices and one detecting device.

If fewer devices are operated in emitting mode, the constant current source output current may be adjusted if it is desirable for the current through the individual UVLEDs to be unchanged or remain below a certain limit.

According to some implementations, multiple bias sources, e.g., multiple constant current sources, are used so that each device (or group of devices) is associated with a separate bias source. It will be appreciated that each device may comprise one UVLED or multiple UVLEDs connected in parallel and/or series. If each device can be coupled to a separate bias source through a separate device "channel," each device channel is isolated from electrical current changes in other device channels. Each device can be set to a different bias current if desired. Setting each device to a different bias current may be useful, for example, to accommodate different regions in a disinfecting chamber, and/or to accommodate devices that are in different states of degradation.

In this particular embodiment, the switches S1-S12 are electromagnetically activated to electrically isolate the relatively high power of the bias source 223 from the relatively lower power components of the switching circuitry, e.g., microprocessor 224 and transistors T1-T6. An alternate switching control approach, such as optically activated switches, could be used in place of the magnetically activated switches to provide electrical isolation between the relatively higher and lower power components of the system.

In the example shown, when the UVLEDs 1-6 are coupled to the bias source 223 through the switches S1-S12, the UVLEDs 1-6 are forward biased and operate in emitting mode. When the UVLEDs 1-6 are decoupled from the bias source 223, the UVLEDs 1-6 are unbiased and operate in detecting mode. Switches S1, S3, S5, S7, S9, S11 operate to couple or decouple the anode of the UVLEDs 1-6 to or from the positive terminal of the bias current source 223. Switches S2, S4, S6, S8, S10, S12 operate to couple or decouple the cathode of the UVLEDs 1-6 to or from the negative terminal of the bias current source 223.

The cycling circuitry 224 controls the switching circuitry to couple and decouple the bias source 223 from the UVLEDs 1-6 according to a sequence that changes the operation of at least some of the UVLEDs 1-6 from emitting mode to detecting mode. The UVLEDs 1-6 may be coupled and decoupled to the bias source one at a time, and/or according to any pattern. In this particular implementation, the sequence of switching the mode of the UVLEDs 1-6 during a cycle and the timing of various periods of the cycle is controlled by microprocessor 224. Outputs 1-6 of the microprocessor 224 are respectively coupled through resistors to the bases of transistors T1-T6 which operate as semiconductor switches. The collectors of the transistors T1-T6 are respectively coupled through inductors RC1-RC12 to the positive voltage of the power supply for the switching control circuitry, indicated as V+ in FIG. 2A. The emitters of the transistors T1-T6 are coupled to ground. Inductors RC1 through RC12 electromagnetically control the position of the switches S1 through S12, respectively, such that when current above a predetermined level flows through the inductors RC1 through RC12, the switches S1-S12 are in a first position and when no current or current below the predetermined level flows through the inductors RC1-RC12, the switches S1-S12 are in a second position.

Using microprocessor output 1 as an example applicable to all other outputs 2-6, when output 1 is in a first state, e.g., a "logic high" state, transistor T1 is turned on causing current to flow through the inductors RC1 and RC2. The current through inductor RC1 and inductor RC2 operates switches S1 and S2, respectively, causing the switches S1, S2 to decouple the anode and cathode of UVLED 1 from the bias source 223. When output 1 is in a second state, e.g., a "logic low" state, transistor T1 is turned off and minimal current flows through the inductors RC1 and RC2 causing switches S1 and S2 to couple the anode and cathode of UVLED 1 to the bias source 223. As shown in FIG. 2A, flyback diodes FD1-FD6 may be used to reduce the sudden voltage spike seen across the inductors RC1-RC12 when the current through the inductors RC1-RC12 is suddenly reduced.

When a UVLED is unbiased or reverse biased, it may act like a photovoltaic cell, when coupled to the appropriate circuitry, the UVLED generating current in response to radiation that falls on the radiation sensitive surface of the UVLED. In the embodiment shown in FIGS. 2A and 2B, the detection circuitry of system 200 includes a trans-impedance amplifier circuit 230 configured to convert the current generated by the UVLED detector to a detection output voltage, $V_d$. FIG. 2A shows a configuration in which the UVLEDs have no bias voltage applied when switched into detection mode. A reverse bias may be applied by use of a pull-up resistor at the minus input of the transimpedance amplifier 230.

The output of the trans-impedance amplifier 230, $V_d$, can be coupled to an input of microprocessor 224. The microprocessor can analyze the output of the trans-impedance amplifier to detect the condition of the UVLEDs operating as emitters, e.g., a low radiation emission condition. The microprocessor 224 may trigger an alarm after the low radiation emission condition is detected. In some embodiments, the microprocessor may be configured to generate a feedback signal based on analysis of the detection output, $V_d$. The feedback signal can cause an increase or decrease in the amount of forward bias current provided by the bias source through the UVLEDs, thereby increasing or decreasing the radiation intensity output of the UVLEDs.

Embodiments described herein can be used in systems that disinfect water or other fluids and can also be used to disinfect structures such as surfaces that come in contact with fluids. In some applications, the system can be used for disinfection of nozzles, spouts, pipes, faucets of water coolers, soda dispensing machines, refrigerator water dispensers, among other structures.

Figure 3:
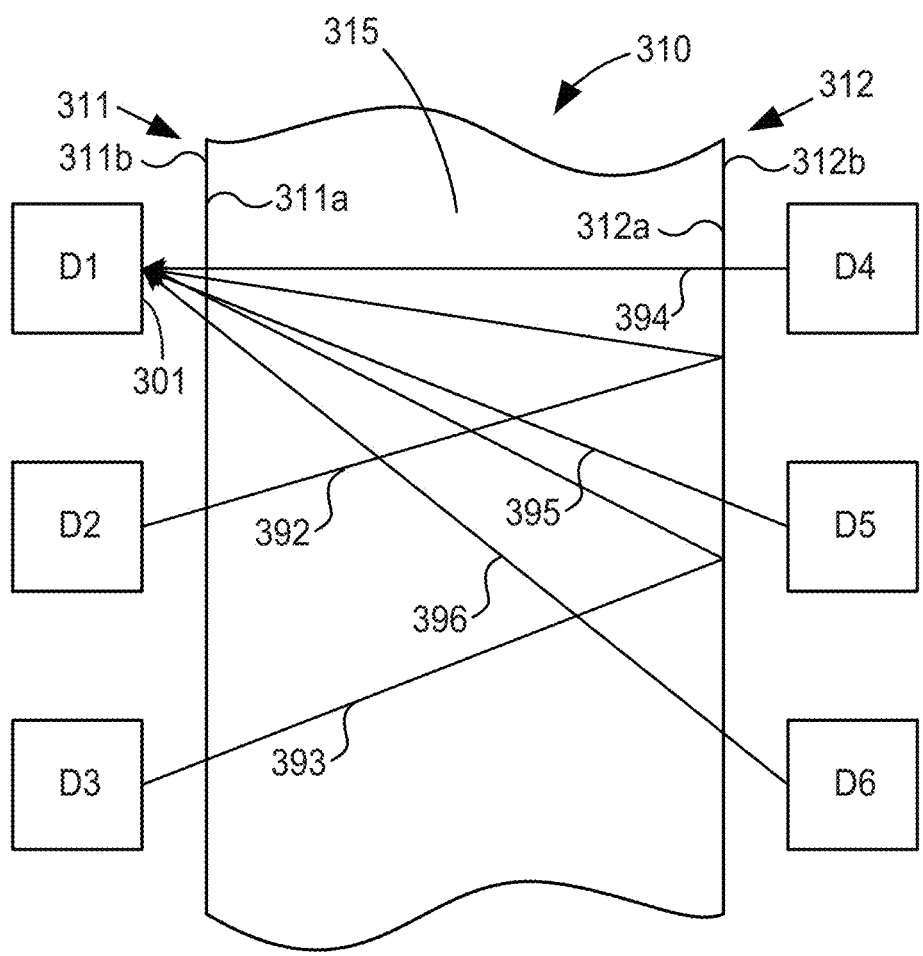
FIG. 3 shows a portion of a structure configured to contain a fluid with short wavelength photonic emitting and detecting devices arranged along one or more fluid containing walls of the structure.

The emitting and detecting devices can be arranged in various ways to disinfect structures and/or fluids. FIG. 3 shows a portion of a structure 310 configured to contain a fluid, e.g., a pipe, a nozzle, or other such device. Devices D1-D6 are arranged along one or more walls 311, 312 of the structure 310, the walls 311, 312 having inner 311a, 312a and outer 311b, 312b surfaces. At least one or more portions of the walls 311, 312 of the structure 310 are transparent to radiation emitted by the devices D1-D6. When operating as emitters, devices D1-D6 emit germicidal radiation through the transparent walls 311, 312 and through the interior 315 of the structure 310. The germicidal radiation may disinfect one or both of the inner 311a, 312a and outer 311b, 312b surfaces of the walls 311, 312. When the interior 315 of the structure 310 contains a fluid, the germicidal radiation may disinfect the fluid as well as one or more of the surfaces 311a, 311b, 312a, 312b.

Cycling circuitry (not shown in FIG. 3, but previously discussed in connection with FIGS. 1 and 2) can be configured to generate a sequence of control signals to control switches to switch the devices D1-D6 between emitting and detecting modes. FIG. 3 shows the operational state of the devices D1-D6 at a point in time during the cycle. At the point in time of the cycle, devices D2-D6 are operating in emitting mode and device D1 is operating in detecting mode. Radiation emitted by devices D4 through D6 is transmitted to the radiation sensitive surface of device D1 as indicated by arrows 394-396. Radiation from devices D2 and D3, e.g., reflected radiation, indicated by arrows 392 and 393, may reach the radiation sensitive surface of device D1. The radiation travels through the transparent walls 311, 312 of the structure 310 and through the interior 315 of the structure 310. Device D1 generates a current in response to radiation emitted by one or more of devices D2 through D6 that falls on the radiation sensitive surface 301 of device D1. It is possible that some radiation emitted by devices D2 and D3 reaches the radiation sensitive surface 301 of D1, contributing to the current generated by D1. However, in many implementations, the arrangement of the devices D1 through D6 would result in radiation from devices D4 through D6 contributing predominately to the current generated by D1. In some embodiments, the system includes a shield so that devices D4-D6 are shielded from ambient radiation to increase the signal to noise ratio of the signal generated by D1 in response to the radiation emitted by D4-D6.

Figure 4:
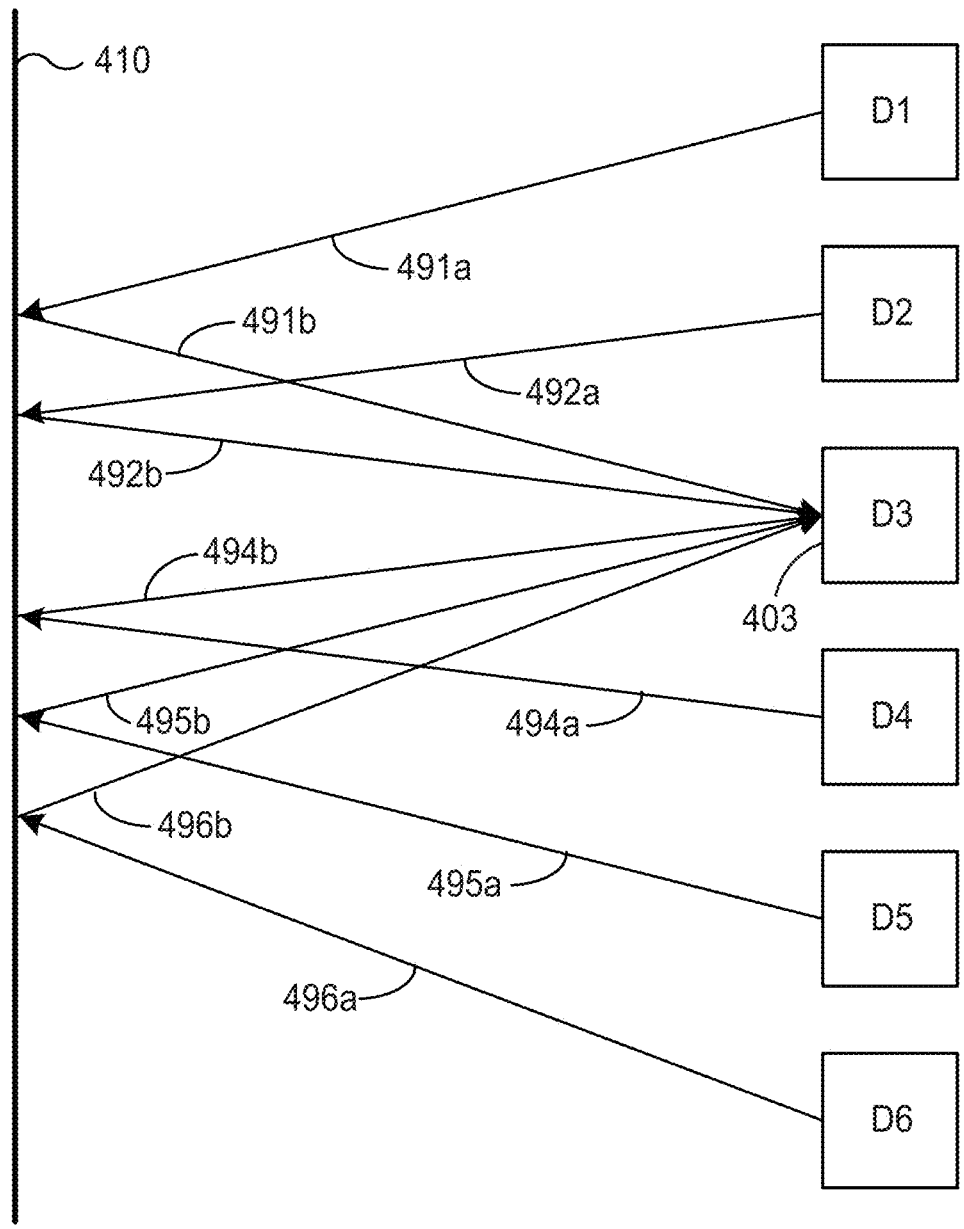
FIG. 4 illustrates short wavelength photonic emitting and detecting devices arranged to disinfect a surface that is at least partially reflective to radiation from the devices.

FIG. 4 illustrates devices D1 through D6 arranged to disinfect a surface 410 that is at least partially reflective to the radiation emitted by the devices D1-D6. When operating as emitters, devices D1-D6 emit radiation of germicidal wavelength and intensity which interacts with microorganisms to disinfect the surface 410 and/or a fluid disposed between the devices D1-D6 and the surface 410. Cycling circuitry (not shown in FIG. 4, but previously discussed in connection with FIGS. 1 and 2) can be configured to control switches to switch the devices D1-D6 between emitting mode and detecting mode. FIG. 4 shows the operational state of devices D1-D6 at a point in time during a cycle. At the point in time of the cycle, devices D1, D2, D4, D5, D6 are operating in emitting mode and device D3 is operating in detecting mode. Radiation emitted by devices D1, D2, D4, D5, D6 (emitted radiation is indicated by arrows 491a, 492a, 494a, 495a, 496a) is reflected by the surface 410 (reflected radiation is indicated by arrows 491b, 492b, 494b, 495b, 496b). The reflected radiation falls on the radiation sensitive surface 403 of device D3 and, in response, device D3 generates a current.

Figure 5A:
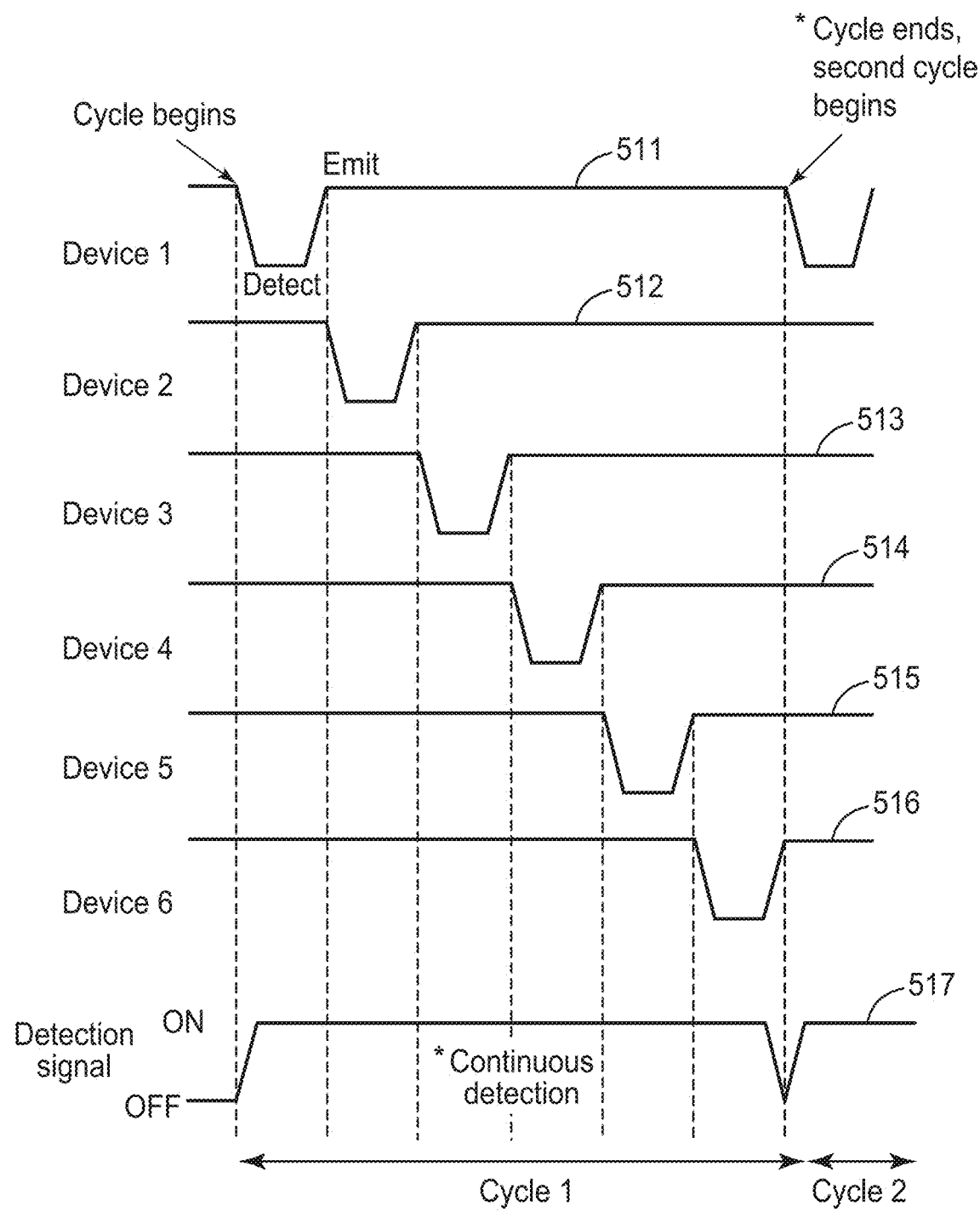
FIGS. 5A and 5B provide examples of timing diagrams of device modes and detection signals in accordance with some embodiments.
Figure 5B:
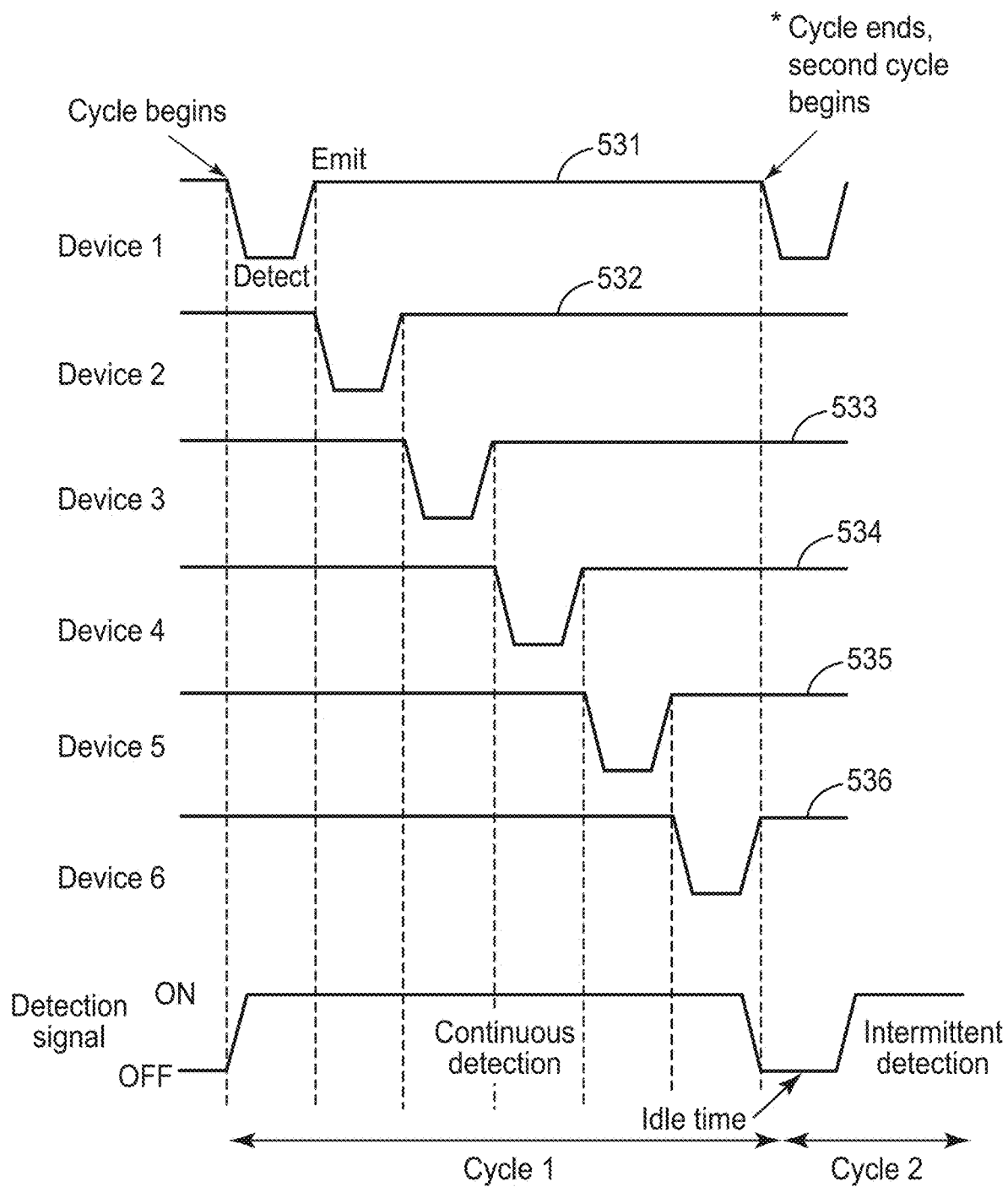

FIGS. 5A and 5B provide example timing diagrams illustrating the modes of six devices D1-D6 during cycles, e.g., devices D1-D6 shown in FIGS. 2, 3 and/or 4. FIGS. 5A and 5B each show a full first cycle, denoted cycle 1, and a portion of a second cycle, denoted cycle 2. In FIG. 5A, during the first cycle, the devices D1 through D6 are cycled one-by-one from emitting mode to detecting mode for a detection time, $t_d$. Each device D1-D6 operates in detecting mode for a detection time, $t_d$, during the cycle. In the example of FIG. 5A, for cycle 1, the total cycle time is $t_c=6t_d$. The idle time that the devices D1-D6 all operate in emitting mode, denoted $t_i$, in this example is zero. The first cycle and the partial second cycle illustrated in FIG. 5A do not include an idle time in which all the devices D1-D6 are emitting.

In the example timing diagram of FIG. 5B, the first cycle is identical to the first cycle of FIG. 5A. The total cycle time for the first cycle of FIG. 5B is $t_c=6t_d$ where $t_i=0$. However, the second cycle of FIG. 5B includes an idle time at the beginning of the second cycle, therefore, for the second cycle, $t_i \ne 0$.

A device, e.g., a. UVLED, is switched to detection mode, held in that mode for a specific period of time, and then switched back to the emitting mode before it is again switched to the detection mode, e.g., at the start of the next cycle. This process is schematically shown in the first cycles of FIGS. 5A and 5B for the example scenario in which there are six devices and each device is switched to detection mode one-by-one such as indicated by graphs 511-516 (FIG. 5A) and 531-536 (FIG. 5B). In the first cycles of FIGS. 5A and 5B, detection is continuous throughout the cycle, as indicated by the detection signal 517 in FIG. 5A. However, there may be embodiments where the detection is intermittent—for example, by having an idle time $t_i$ in a cycle where none of the devices are in detection mode as indicated by the second cycle of FIG. 5B. At the beginning of the second cycle of FIG. 5B, there is an idle time in which all of the devices D1-D6 are emitting. It will be appreciated that the idle time can be at the beginning of the cycle, the end of the cycle, and/or can comprise the sum of idle times that occur in between the detection periods of the devices during a cycle.

Generally, the cycle time is the sum of the device detection times for each device added to the idle time, $t_i$. Expressed mathematically, the cycle time, $t_c$ is:

$$t_c = \sum_{j=1}^{n} t_{d,j} + t_i,$$

where n is the total number of devices $t_d$ is the detection time for a particular device, and $t_i$ is the idle time. The percent ON time for a device then becomes:

$$\% \ t_{ON} = 100\left(1 - \frac{t_d}{t_c}\right).$$

For example, in some implementations, six devices are used with $t_d$ and $t_i$ both equal to 4 s. Thus, % $t_{ON}$ for each device becomes about 86%, i.e. each device was emitting 86% of the time.

If $t_i=0$ and $t_d$ for each device is the same, then the $$\% \ t_{ON} = 100\left(1 - \frac{1}{n}\right),$$

i.e. the % $t_{ON}$ for each device is a function of n only. For n=2, 3, and 4, % $t_{ON}$ will be 50, 67, and 75%, respectively—i.e. higher the number of devices, longer each device is in the emitting mode. If $t_i \ne 0$, % $t_{ON}$ will be even higher.

Note that various aspects of a cycle, e.g., cycle time, detection time, idle time, and/or other aspects can be adjusted to desired values. Each of the devices need not have the same detection time during a cycle and/or time intervals between devices that are switched to detection mode may vary during a cycle or from cycle to cycle. When the detection periods of the devices are equal during a cycle, the detection periods are referred to as "regular" and when the detection periods of at least some of the devices are unequal during a cycle, the detection periods are referred to as "irregular." The number and/or pattern (one-by-one, two-by-two, etc) of devices switched to detection mode, the detection times of the devices, cycle times, idle times, and/or other aspects may vary within a cycle and/or from cycle-to-cycle.

Figure 6:
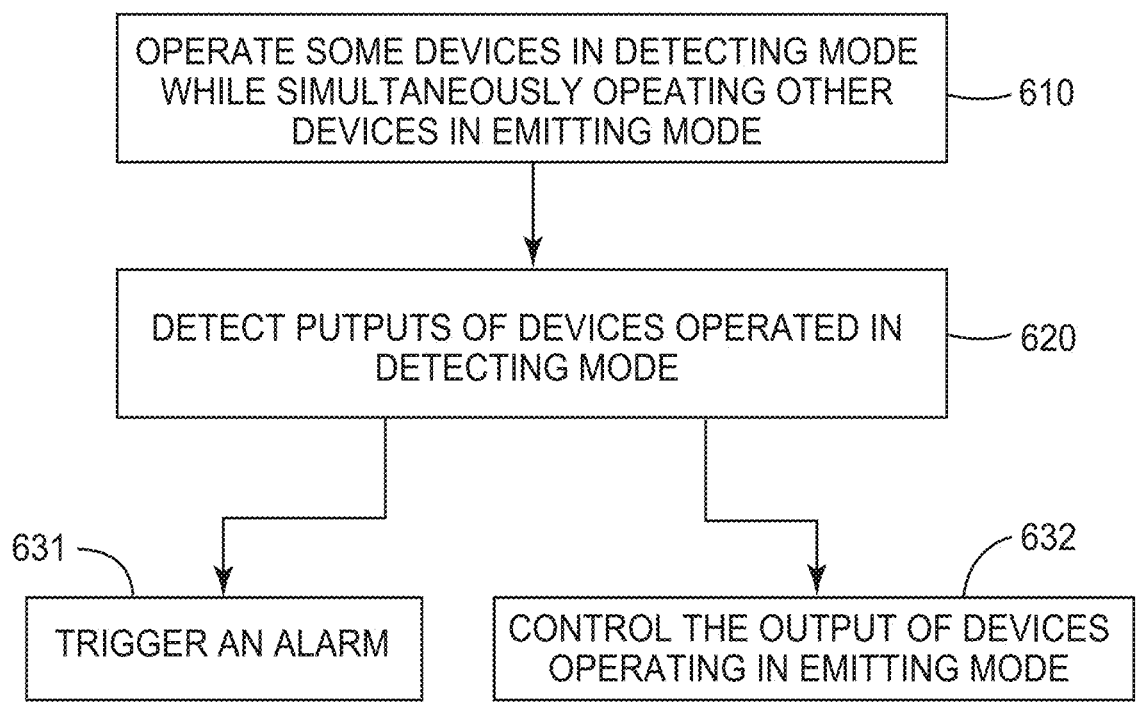
FIG. 6 is a flow diagram illustrating a method of operating multiple emitting and detecting devices in accordance with some embodiments.

FIG. 6 is a flow diagram illustrating a method of operating multiple emitting and detecting devices in accordance with some embodiments. Multiple devices capable of emitting and detecting are operated 610 in a cycle in which at least some of the multiple devices are sequentially switched to detecting mode during each cycle while other devices simultaneously operate in emitting mode. Each device of the multiple devices, when operating in detecting mode, senses radiation emitted by at least one of the multiple devices operating in emitting mode. Each device of the multiple devices operating in detecting mode during the cycle generates a signal responsive to the sensed radiation. The signals of the devices operating in detecting mode that are responsive to the sensed radiation are detected 620 and a detection output for the cycle is generated in response to the detected signals. The detection output indicates a radiation intensity received from the devices that operate in emitting mode.

Various processes can be implemented based on the detection signal. For example, in some embodiments, the detection signal may trigger 631 an alarm that indicates a low radiation intensity condition. In some embodiments, a feedback signal may be generated 632 that increases or decreases the radiation emitted by the devices.

The feedback signal allows for adjustments in the radiation intensity based on system demand. For example, in fluid disinfecting systems, decreased UV transmittance of the fluid places an increased demand on the system. As illustrated in the arrangement illustrated in FIG. 3, the turbidity of fluid in the structure may cause a decrease in the radiation reaching the device or devices operating as detectors. In this situation, the decreased intensity sensed by the detectors would cause the monitoring/control circuitry to increase the radiation emitted by the devices operating as emitters.

Figure 7:
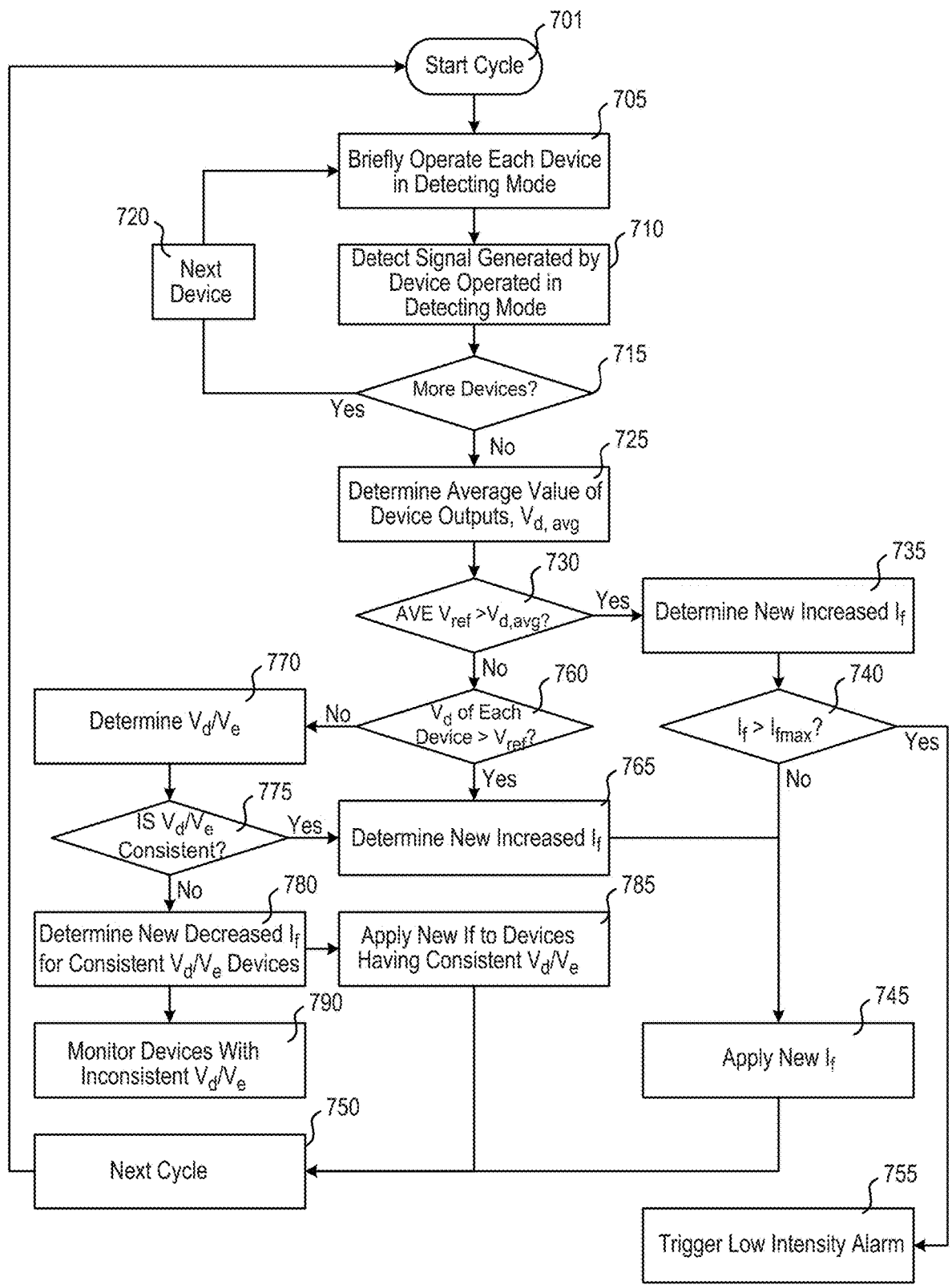
FIG. 7 is a flow diagram illustrating a method of operating a system that includes multiple emitting and detecting devices in accordance with some embodiments.

FIG. 7 is a flow diagram illustrating a method of operating a system (such as the system illustrated in FIGS. 2A and 2B) that includes multiple emitting and detecting devices in accordance with some embodiments. During a cycle 701, one or more of the devices are operated 705 for a brief time in detecting mode according to a sequence while other devices are operated in emitting mode. The device operated in detecting mode senses radiation emitted by some or all of the devices that operate as emitters. The detector generates a current in response to the sensed radiation. The current generated by the detector is detected 710 by detection circuitry and converted to a detection signal, $V_d$. For example, in some implementations, a trans-impedance amplifier converts the current generated of each UVLED operating as an emitter to a detection voltage, $V_d$, as previously discussed. The devices are operated 715, 720 as detectors according to the sequence until the cycle is complete.

Monitoring/control circuitry can perform various operations based on the detection signal, $V_d$. For example the detection signal may be monitored to identify low emission conditions. As another example, the current that forward biases the devices when they operate as emitters can be increased or decreased based on the detection signal.

In the embodiment of FIG. 7, the monitoring/control circuitry determines 725 the average value of the detection signal produced by the devices operated in detection mode. For example, the average value of the detection signal, $V_d$, is the average value of the detection output which includes contributions from each of the devices when they operate in detecting mode. The detection output contributions of devices 1-6 are expressed respectively as $V_{d1}$ through $V_{d6}$. The average value, $V_{d,avg}$, of the detection signal is compared 730 to an average reference value, AVE $V_{ref}$. If the average reference value AVE $V_{ref}$ is greater than $V_{d,avg}$, then a new increased forward bias current, $I_f$, is determined 735. For example, the value of the new increased forward bias current may be determined based on a difference between AVE $V_{ref}$ and $V_{d,avg}$. If the increased forward bias current is less than or equal to 740 a maximum forward bias current, $I_{fmax}$, then the new forward bias current is applied 745 to the devices operating as emitters during 750 one or more subsequent cycles, e.g. starting with the next cycle. The increased forward bias current causes increased emission from the devices when they are operated as emitters. However, if the increased forward bias current is greater than the maximum forward bias current, an alarm is triggered 755 indicating a low intensity condition.

If the average reference value AVE $V_{ref}$ is less than or equal to $V_{d,avg}$, then the detection output, $V_{dx}$, contributed for each device, x, when operated as a detector is compared 760 to its individual reference value, $V_{refx}$, where x may be an integer between 1 and 6 for the embodiments illustrated in FIGS. 2, 5A and 5B, for example. If, for all devices, the detection output, $V_{dx}$, produced by the device when operated as a detector is greater than its individual reference value, $V_{refx}$, then a new decreased forward bias current is determined 765 and applied 745 to the devices operating as emitters during 750 one or more subsequent cycles, e.g., starting with the next cycle. The decreased forward bias current causes decreased emission from the devices when they are operated as emitters.

If the detection output, $V_{dx}$, contributed by any device x when operated as a detector is less than or equal to its individual reference value, $V_{refx}$, then the ratio $V_{dx}/V_{ex}$ is determined 770 for each device, where $V_{ex}$ is the voltage drop across the device when the device operates as an emitter. If the ratio $V_{dx}/V_{ex}$ is consistent 775 for each of the devices such that the cycle-to-cycle variation in the ratio $V_{dx}/V_{ex}$ for each device is within a specified range, e.g., below a variability reference value, then a new decreased forward bias current is determined 765 and applied 745 to the devices operating as emitters during 750 one or more subsequent cycles, e.g., starting with the next cycle. The decreased forward bias current causes decreased emission from the devices when they are operated as emitters.

Using the ratio $V_d/V_e$ to determine the health of a device is particularly useful. When an UVLED used as an emitter, there will be a characteristic threshold/turn-on voltage across the UVLED. At or above this characteristic threshold/turn-on voltage, the UVLED enters its linear operating region, in which the optical output is proportional to the input current. This voltage across the device when the device operates as an emitter is the basis for $V_e$. If the UVLED temperature becomes excessive (for example) or if the UVLED semiconductor is degraded by defects, aging, static electricity or overbiasing, $V_e$ may be degraded or unstable. In some scenarios, when $V_e$ is degraded or unstable, the UVLED fails to operate.

When properly configured as a detector, an output current is generated, which is proportional to the detected light intensity. This current is converted to a voltage ($V_d$) by subsequent transimpedance and conditioning circuitry. If there is degradation of the semiconductor, the proportionality of $V_d/V_e$ is impacted.

In a healthy UVLED, there should be a specified relationship between the $V_d$ and $V_e$. The precise value of $V_e$ will vary from UVLED to UVLED and may vary with forward bias current and temperature, but will be predictable for a given set of conditions. The precise value of $V_d$ may also vary based on conditions, but it is generally predictable as well.

The $V_d/V_e$ ratio for a given device can be determined and utilized for device health diagnostics and performance compensation. This ratio scales well and is predictable for a given set of operating conditions in a healthy device, even though the individual $V_d$ and $V_e$ values are not identical from device to device. If the device starts to degrade, the output current in the detector mode may decrease, thus reducing the level of $V_d$. If an electrical spike damages the semiconductor, $V_e$ may degrade significantly. Using the ratio approach, such cases can be identified.

If the ratio $V_{dx}/V_{ex}$ is inconsistent for at least one of the devices such that the cycle-to-cycle variation in the ratio $V_{dx}/V_{ex}$ of at least one device is outside the specified range, e.g., above the variability reference value, then a new reduced forward bias current, $I_f$ is determined 780 and applied 785 to the devices for which the $V_{dx}/V_{ex}$ ratio is consistent during 750 one or more subsequent cycles, e.g., starting with the next cycle. The forward bias current $I_f$ is not changed (or may be increased) for the at least one inconsistent device during the next and/or subsequent cycles. The device with inconsistent ratio $V_{dx}/V_{ex}$ is monitored 790 during subsequent cycles. If the variation in the $V_{dx}/V_{ex}$ ratio increases over subsequent cycles, this may indicate degradation of the device, and an error signal may be generated by the monitoring/control system.

As described above, in some embodiments, the radiation from multiple devices operating as emitters during a time period is detected by a single device operated as a detector and multiple devices operate as detectors during the time period. In this scenario, the detection output contributed by the single device operating as a detector is produced from radiation emitted by all the devices that operate as emitters during the time period. In some embodiments, the emission of each device may be individually checked. For example, consider the arrangement illustrated in FIG. 3. The cycle may include a first time period in which D1 operates as a detector, D4 operates as an emitter, and devices D2, D3, D5, and D6 do not emit radiation and are disconnected from the detection circuitry such that the detection signal $V_d$ is produced only by D1. The cycle may include a second time period in which D2 operates as a detector, D5 operates as an emitter, and devices D1, D3, D4, and D6 do not emit radiation and are disconnected from the detection circuitry such that the detection signal $V_d$ is produced only by D2. The cycle may include a third time period in which D3 operates as a detector, D6 operates as an emitter, and devices D1, D2, D4, and D5 do not emit radiation and are disconnected from the detection circuitry such that the detection signal $V_d$ is produced only by D3. The cycle may include a fourth time period in which D4 operates as a detector, D1 operates as a emitter, and devices D2, D3, D5, and D6 do not emit radiation and are disconnected from the detection circuitry such that the detection signal $V_d$ is produced only by D4. In this scenario, the emission output of each device can be individually determined by the monitoring circuitry from the detection signal.

In some arrangements multiple devices may operate as detectors with a single device operating as an emitter to check the output of the single device using multiple detectors. In some embodiments, devices may be coupled to separately controllable forward bias sources so that a different forward bias current can be applied to each device when the device operates as an emitter. As another example, the current generated by each of the devices can be detected by a separate transimpedance amplifier (or other detection circuit) or the output of the device can be time multiplexed by a multiplexer to a single detection circuit allowing the individual outputs of each device operated as detector during the same time period to be separately detected.

In some embodiments, current generated by first and second adjacent devices operated as detectors during different time periods (or the same time period) could be used to cross-check each other as detectors. It would be expected that adjacent devices of similar construction would produce a similar current in response to the same radiation intensity and/or that the output currents of the two adjacent devices operating as detectors would remain repeatable under the same radiation conditions. A change in the output of the first device relative to the output of the second device may indicate degradation of the first device.

In some scenarios, it may be useful to discriminate between gradual degradation and an abrupt degradation, e.g., catastrophic failure, of the emitters. The cycle to cycle average value of the detection output can be monitored and/or stored over time. Additionally or alternatively, the cycle to cycle value of the detection output contribution of each individual device can be monitored and/or stored over time. Gradual degradation may be detected when there is a gradual decrease over time in the average values of detection signal and/or a gradual decrease over time in one of more of the detection outputs. An abrupt degradation may be detected when a decrease having a magnitude greater than a predetermined amount is detected.

EXAMPLES

Experimental Method

An experimental apparatus was built to demonstrate the working of the performance monitoring system. The apparatus consists of UVLEDs 1-6 mounted in an assembly as shown in FIG. 8, electrical circuitry (see FIGS. 2A and 2B), including a constant current source to power the UVLEDs, and instrumentation (e.g. oscilloscope) to measure and record the detected signals.

Figure 8:
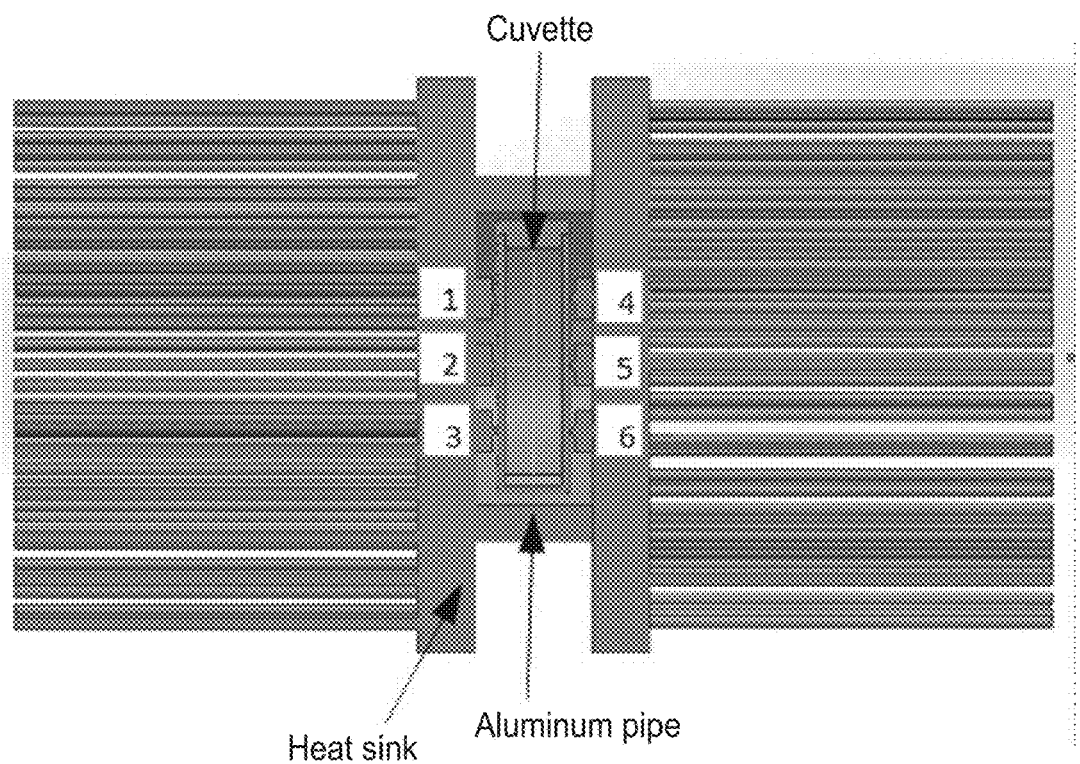
FIG. 8 shows an experimental apparatus built to demonstrate the working of a system according to some embodiments.

The assembly contains six UVLEDs that were mounted facing each other with a fused silica cuvette in between, as shown in FIG. 8. The UVLEDs were obtained from Crystal IS (Troy, N.Y.) and emit radiation in the UVC spectrum (240-280 nm). The UVLEDs could be driven with currents as high as 300 mA with corresponding radiation outputs up to 13 mW. The cuvette could be filled with water to mimic behavior of UV transmission in a UV water purifier. The UVLEDs were mounted onto heat sinks with the help of a thermal tape in order to prevent them from overheating. A short piece of aluminum pipe was put around the UVLEDs to act as a shield against UV radiation.

The electrical circuitry used to exemplify the performance monitoring system is as shown in FIGS. 2A and 2B. The circuit serves multiple purposes: a) it provides a constant current source to the UVLEDs, b) it switches the UVLEDs at a desired frequency between emitting and detecting modes, c) it cycles the UVLEDs one-by-one into the detection mode at a desired frequency, and d) it conditions the signal generated by the UVLEDs. The current source was provided by a constant current power supply. The switching and cycling signals were generated by a microcontroller, which could vary the signal frequency to desired values. Transistors T1-T12 (2N4401) and Reed switches S1-S12 (see FIGS. 2A and 2B) were used to interface the low-power microcontroller circuit with the relatively high-power current source circuit. The current signal generated by the UVLEDs operating in current detection mode was amplified and conditioned using a trans-impedance amplifier and capacitor, giving a desirable output signal.

An oscilloscope was used to display and record the output signal. The drive current for the UVLEDs could be set on the power supply to a desired value and was also confirmed by precision current meters.

The measured output signals at the output of the trans-impedance circuit ($V_d$) were correlated to UV intensity (mW/cm$^2$) using a UV spectroradiometer. The radiometer sensor was put in place of each UVLED one-by-one to measure the UV intensity that would fall on the UVLED and the intensity as well as spectrum of the incident radiation was recorded.

Example 1

Figure 9:
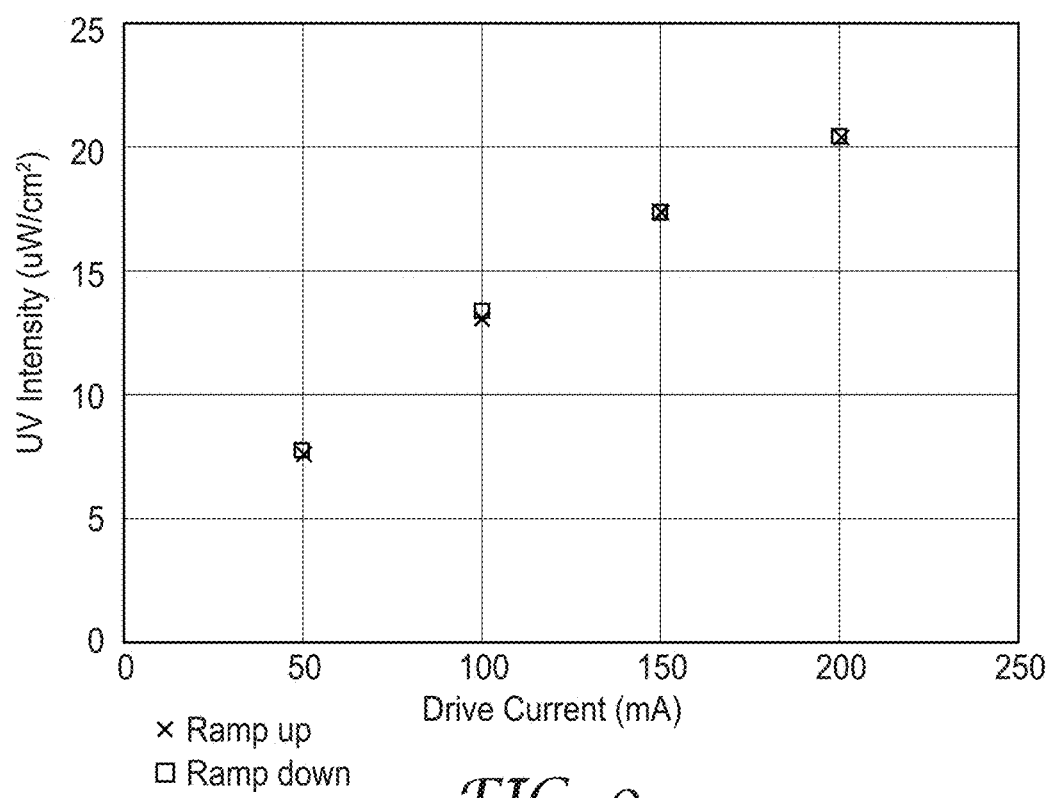
FIG. 9 is a graph showing ultraviolet (UV) intensity as a function of ultraviolet light emitting diode (UVLED) drive (forward) current during continuous ramp up followed by ramp down.

This experiment was conducted to determine if the UV intensity (i.e. irradiance) could be increased or decreased, without any hysteresis, by directly varying the drive (forward) current applied to the UVLED. The apparatus of FIG. 8 was used, with the detector of the spectroradiometer put in place of the UVLED4. The drive current to UVLED1 was varied between 50-200 mA and the results are shown in FIG. 9. FIG. 9 is a graph showing UV intensity, measured by the spectroradiometer, as a function of UVLED drive (forward) current during continuous ramp up followed by ramp down. It can be seen that the measured UV intensity, emitted by the UVLED1, varies almost linearly with the drive current. Furthermore, there is no hysteresis in the UV intensity when the current was ramped up followed by a ramp down. Such behavior facilitates on-demand control of UV intensity in an application by changing the drive current.

Example 2

Figure 10:
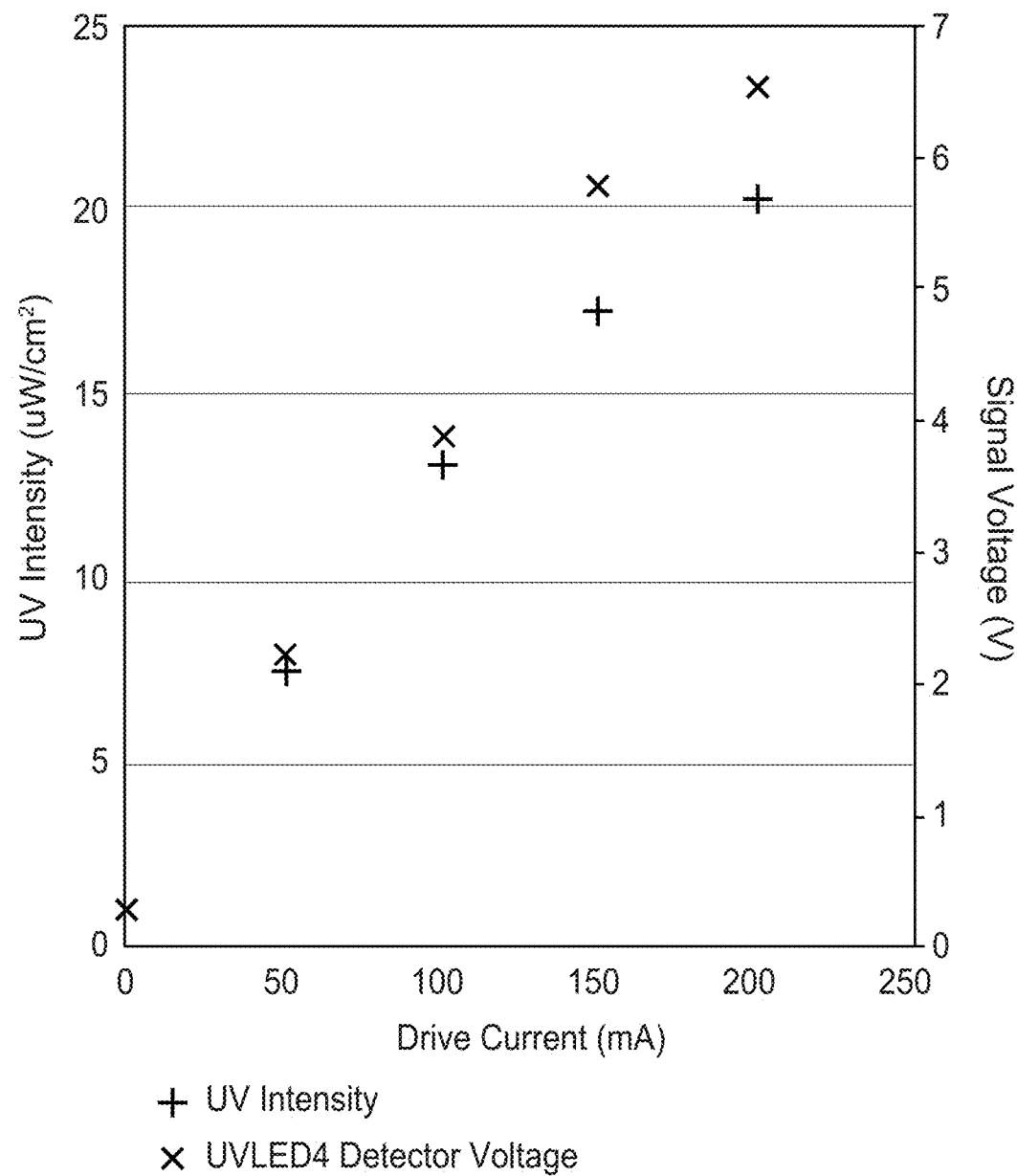
FIG. 10 shows the measured UV intensity and the signal voltage, with UVLED4 in detecting mode, as a function of drive current to UVLED1.

In this experiment, UVLED1 was used as emitter while UVLED4 was used as a detector. The drive current to UVLED1 was varied from 50 to 200 mA and the signal voltage generated by UVLED4 was measured at the output of the trans-impedance amplifier. The results are shown in FIG. 10, which shows the measured UV intensity and the signal voltage, with UVLED4 in detecting mode, as a function of drive current to UVLED1. FIG. 10 reveals that the signal voltage increases with the drive current, similar to what was seen for the UV intensity. This data demonstrates that higher the UV intensity incident upon the detecting UVLED, higher the output signal that it generates.

Example 3

Figure 11:
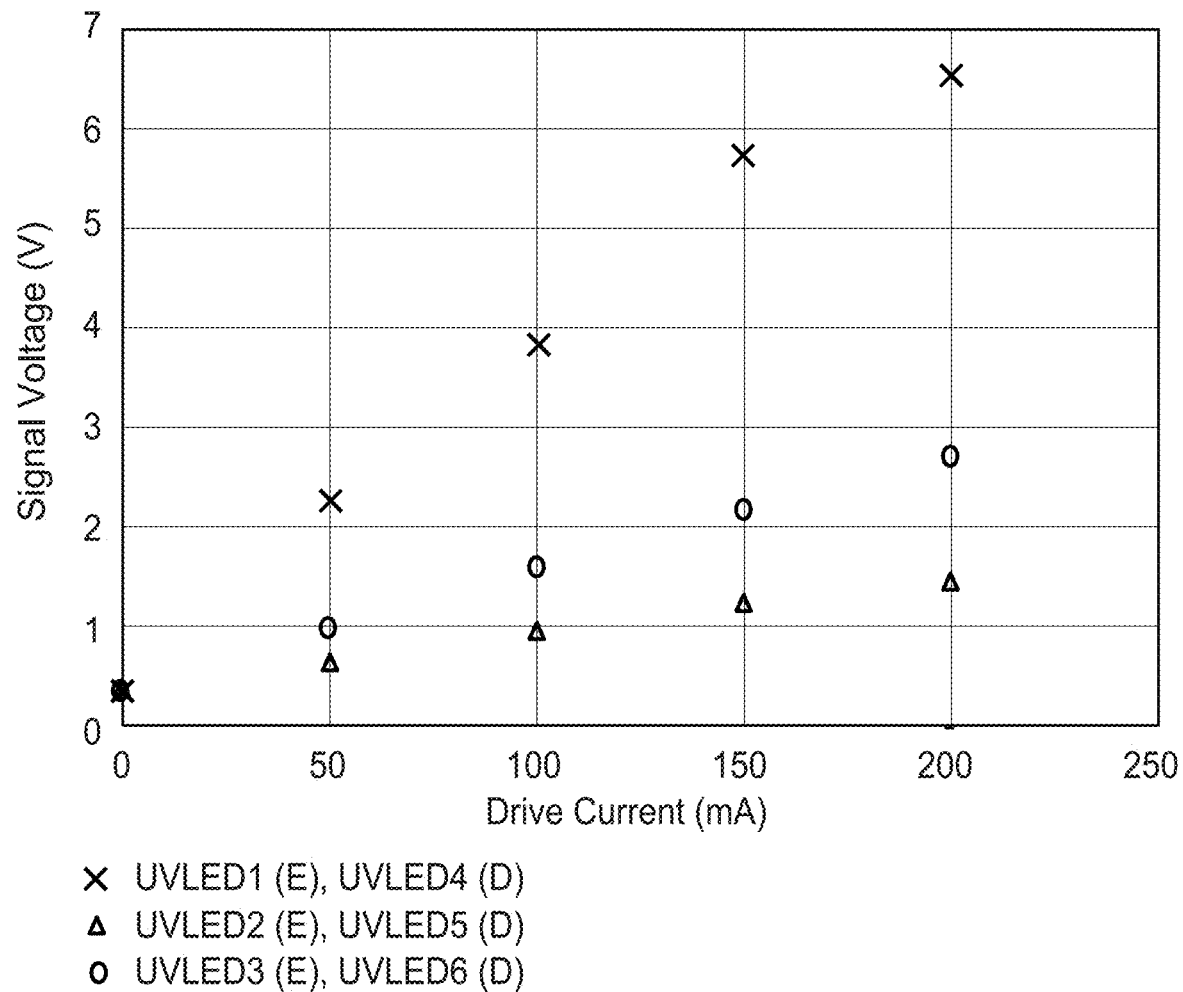
FIG. 11 shows the measured signal voltage as a function of drive current for different UVLEDs.

The experiment of Example 2 was repeated for other UVLEDs to demonstrate that the ability of UVLED1 to function as a detector was general and therefore could be extended to other UVLEDs too. For this purpose, UVLEDs 5 and 6 were put in the detection mode while UVLEDs 2 and 3 were put in the emitting mode, respectively. The resulting data is shown in FIG. 11, which provides the measured signal voltage as a function of drive current for different UVLEDs. FIG. 11 reveals that the measured signal voltage increases with the drive current. The voltages from different UVLEDs, however, could be different due to the intrinsic (crystal structure, defects, etc.) differences in their construction, power (rated as well as diminishment with use) and, in the present experiment, their alignment to each other.

Example 4

Figure 12:
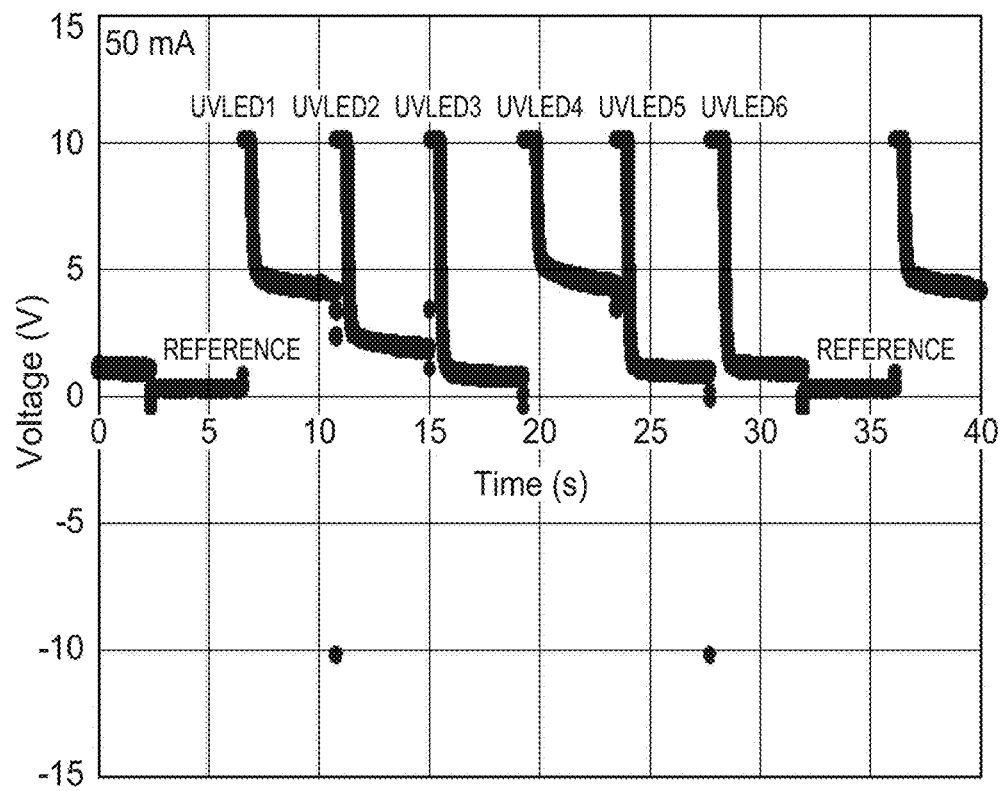
FIG. 12 shows the signal measured at the output of the trans-impedance amplifier with an empty cuvette.

The above experiments were conducted with only one UVLED as emitter and the other as a detector. This experiment was done with multiple UVLEDs working simultaneously as emitters and detectors, with switching and cycling modes. There was no water in the cuvette. The drive current for each UVLED was set at 50 mA. The detection time for each UVLED was set to 4 seconds, totaling 24 seconds for the six UVLEDs. The idle time was also 4 s, giving a total cycle time of 28 seconds. Data was recorded four times to confirm repeatability. The output signal as measured at the output of the trans-impedance amplifier is shown in FIG. 12. FIG. 12 indicates that when all UVLEDs are emitting, the output signal is low (labelled as 'Reference') with a value of about 0.34 V. As soon as UVLED1 is switched to detection mode, the output signal increases immediately and quickly decays down to settle at a steady-state value of about 4 V. Next, UVLED2 is switched to the detection mode and the output signal behaves in a similar manner to give a steady-state value of about 2 V, and so on until all of the remaining UVLEDs are switched to the detection mode one-by-one thereby completing a full cycle when the output signal falls back to the reference value.

Example 5

Figure 13:
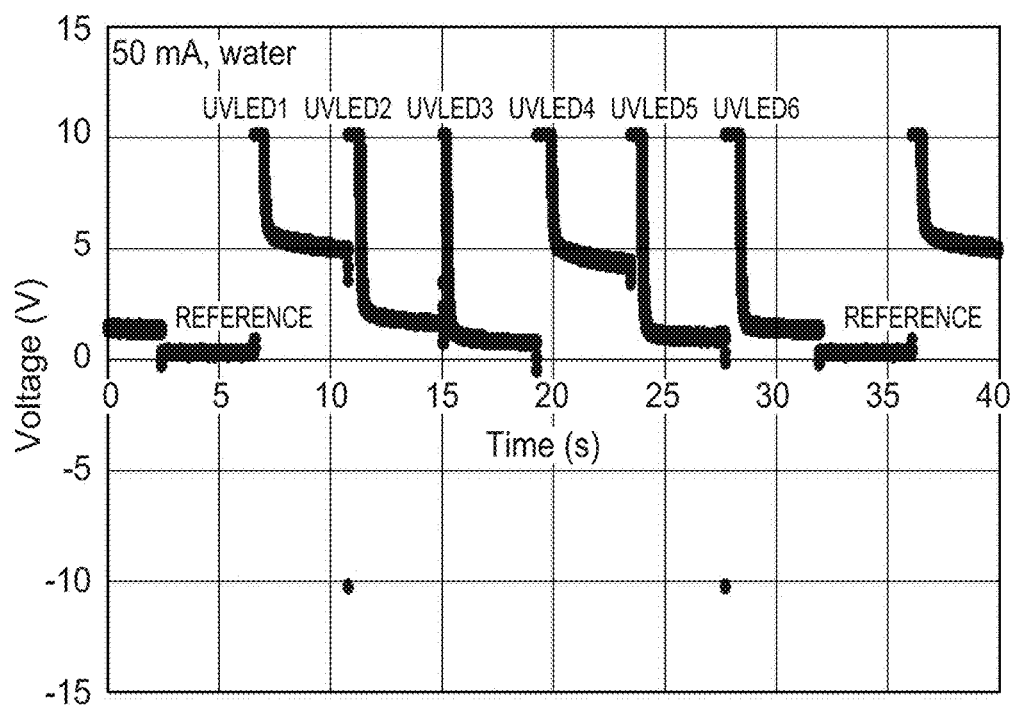
FIG. 13 shows the signal measured at the output of the trans-impedance amplifier with water in the cuvette.

This experiment was similar to the one described in Example 4 except that it was conducted with water in the cuvette. The output signal as measured at the output of the trans-impedance amplifier is shown in FIG. 13. The drive current for each UVLED was set at 50 mA. The output signal shown in FIG. 13 indicates that the overall behavior of the output signal is very similar to that of Example 4 suggesting that the concept disclosed in this invention works equally well when the intervening medium is water.

Example 6

Figure 14:
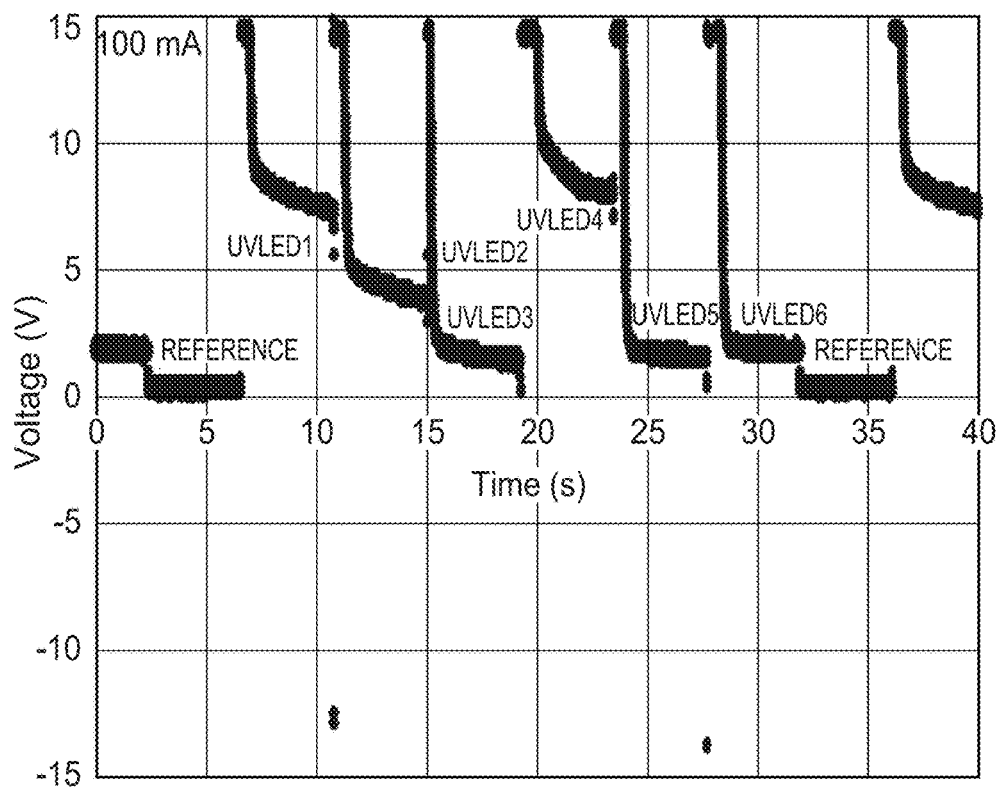
FIG. 14 shows the output signal as measured at the output of the trans-impedance amplifier with an empty cuvette and a drive current for each UVLED of 100 mA.

This experiment was the same as the one described in Example 4 except that the drive current for UVLEDs was set at 100 mA. FIG. 14 shows the output signal as measured at the output of the trans-impedance amplifier. The output signal shown in FIG. 14 indicates that the overall behavior stays similar to that in Examples 4 and 5, but the amplitude is generally higher due to the higher drive current.

Example 7

Figure 15:
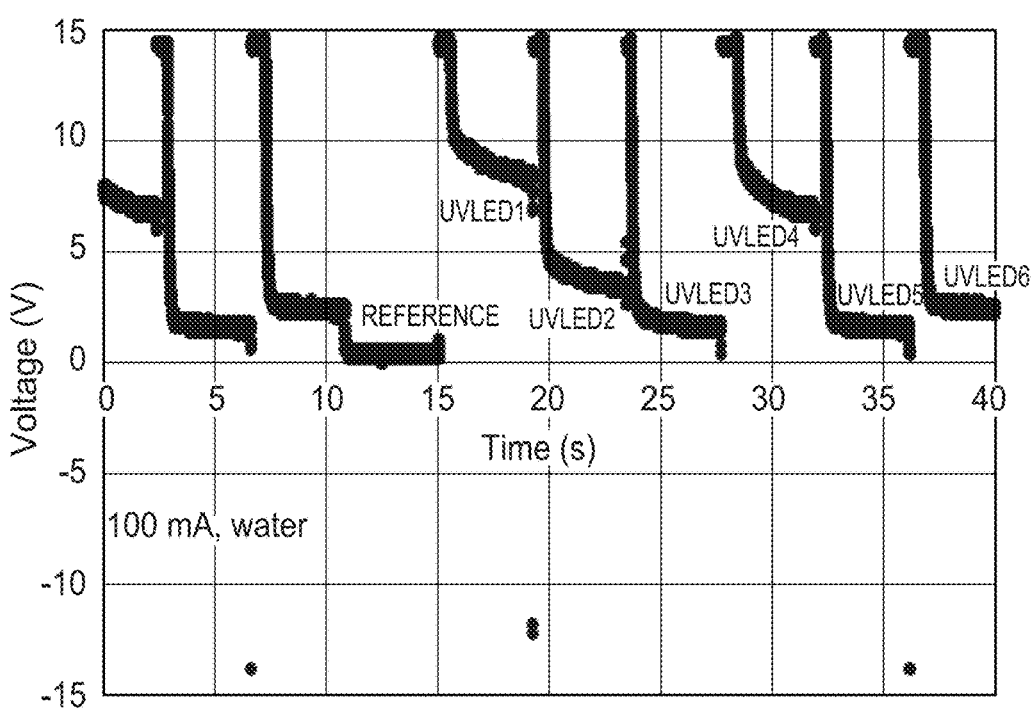
FIG. 15 shows the output signal as measured at the output of the trans-impedance amplifier with water in the cuvette and a drive current for each UVLED of 100 mA.

This experiment was the same as the one described in Example 6 except that the cuvette was filled with water. FIG. 15 shows the output signal as measured at the output of the trans-impedance amplifier. The output signal shown in FIG. 15 indicates that the overall behavior is consistent and repeatable at different drive currents and with or without water in the cuvette.

Approaches disclosed herein have been described in terms of devices, systems, and methods involving UV disinfection, e.g., UV water purification, but are suitable for performance monitoring in other systems that include devices configured to both emitting and detecting radiation. The system simultaneously uses some devices as radiation emitters while using other devices as radiation detectors. When UV light emitting diodes (UVLEDs) are used as the radiation emitting/detecting devices, each UVLED can be operated as an emitter or a detector by switching the UVLED between forward bias and disconnecting from the drive source or connecting in a reverse bias configuration. Features arising from this design include a) dedicated sensors for intensity monitoring are not required, which lowers cost, b) since each device can also function as a radiation sensor, redundancy is built in to the system, thus improving product reliability, c) product operating condition (e.g. drive current) can be actively managed from the intensity feedback generated by the devices, d) false alarms can be reduced by measuring intensity from multiple positions. Embodiments disclosed herein involve radiation emitting and detecting devices, e.g., LEDs or UVLEDs, and operational circuitry that can be used in products within and beyond the water disinfection space.

Items disclosed herein include:

Item 1. A system comprising:

multiple devices configured to operate in radiation emitting mode and radiation detecting mode, each of the devices configured to emit and detect radiation that is germicidal in wavelength and intensity;

at least one drive source, each of the multiple devices configured to operate in emitting mode when connected to the drive source in a forward bias configuration and to operate in detecting mode when disconnected from the drive source or when connected to the drive source in a reverse bias configuration;

switching circuitry coupled to each of the devices and to the drive source;

cycling circuitry configured to generate a sequence of control signals that control the switching circuitry to change the connections of the devices to the drive source in a cycle in which one or more of the multiple devices is switched to detecting mode and senses radiation emitted by one or more of the multiple devices simultaneously operating in emitting mode, each device operating in detecting mode generating a signal in response to the sensed radiation; and detection circuitry configured to detect signals of the devices operating in detecting mode and to generate a detection output in response to the detected signals.

Item 2. The system of item 1, wherein the cycling circuitry is configured to switch each device to operate in detecting mode at least once during the cycle.

Item 3. The system of any of items 1 through 2, wherein the cycling circuitry is configured to switch some but not all of the multiple devices to operate in detecting mode during the cycle.

Item 4. The system of any of items 1 through 3, wherein the cycling circuitry is configured to switch the multiple devices one-by-one to operate in detecting mode during the cycle.

Item 5. The system of any of items 1 through 4, wherein, during each cycle, each device operating in detecting mode is arranged to sense radiation emitted by two or more devices operating in emitting mode.

Item 6. The system of any of items 1 through 5, wherein periods of time that the devices operate in detecting mode during the cycle vary.

Item 7. The system of any of items 1 through 6, wherein:
the cycling circuitry comprises a microcontroller executing programmed instructions; and
the detection circuitry comprises a trans-impedance amplifier.

Item 8. The system of any of items 1 through 7, further comprising monitoring/control circuitry configured to compare the detection output to a predetermined threshold and to generate an alert in response to the detection output being below the predetermined threshold.

Item 9. The system of an of items 1 through 8, wherein:
each device operated in emitting mode during the cycle contributes to the detection output; and
the monitoring/control circuitry is configured to:
determine an average value of the detection output;
compare the average value to an average reference value; and
generate a feedback signal that changes a drive signal of the drive source during a subsequent cycle in response to the average reference value being different from the average value.

Item 10. The system of item 9, wherein the monitoring/control circuitry is configured to:
compare the drive signal to a maximum drive signal; and
trigger an alert in response to the drive signal being greater than the maximum drive signal.

Item 11. The system of item 10, wherein the monitoring/control circuitry is configured to:
compare a detection output contributed by each device to a reference value of the device; and
generate a feedback signal that changes the drive signal of the drive source in response to the detection output contributed by at least one of the devices being different from the reference value of the at least one device.

Item 12. The system of any of items 1 through 11, wherein each device operated in emitting mode during the cycle contributes to the detection output; and
the monitoring/control circuitry is configured to:
determine a variability of each device operating in detecting mode during the cycle using the detection output contributed by the device; and
generate a feedback signal that changes a drive signal of the drive source during a subsequent cycle in response to the variability of at least one of the devices being below a variability reference value.

Item 13. The system of item 12, wherein the monitoring/control circuitry is configured to monitor the device for changes in variability in response to the variability of the device being above the variability reference value.

Item 14. The system of any of items 1 through 13, wherein the devices are arranged so that the radiation emitted by the at least one device operating in emitting mode is reflected from one or more surfaces towards the device operating in detecting mode.

Item 15. The system of any of items 1 through 14, wherein the devices are arranged so that the device operating in detecting mode detects the radiation emitted by the at least one device operating in emitting mode, wherein the radiation is transmitted through one or more containers configured to contain a fluid.

Item 16. A method comprising:
operating multiple devices configured to emitting and detecting radiation that is germicidal in wavelength and intensity in a cycle by generating a sequence of control signals that switch one or more of the multiple devices to detecting mode during the cycle;
each device of the multiple devices, when operating in detecting mode, sensing radiation emitted by one or more of the multiple devices simultaneously operating in emitting mode and generating an electrical signal responsive to the sensed radiation; and
detecting electrical signals of the devices operating in detecting mode and generating a detection output in response to the detected electrical signals, the detection output indicating an intensity of the radiation sensed by the devices operating in detecting mode during the cycle.

Item 17. The method of item 16, wherein operating the multiple devices comprises switching each device of the multiple devices to detecting mode at least once during the cycle.

Item 18. The method of any of items 16 through 17, wherein operating the multiple devices comprises switching some but not all of the multiple devices to operate in detecting mode at least once during the cycle.

Item 19. The method any of items 16 through 18, wherein operating the multiple devices comprises switching the devices one-by-one to operate in detecting mode during the cycle.

Item 20. The method of any of items 16 through 19, further comprising:
comparing the detection output to a predetermined threshold; and
generating an alert in response to the detection output being below the predetermined threshold.

Item 21. The method of any of items 16 through 20, wherein each device operated in emitting mode during the cycle contributes to the detection output, and further comprising:
determining an average value of detection output;
comparing the average value to an average reference value; and
generating a feedback signal that increases or decreases an intensity of radiation emitted by the devices operating in emitting mode during a subsequent cycle in response to the average reference value being different from the average value.

Item 22. The method of item 21, wherein:
the feedback signal changes a drive signal of the drive source during a subsequent cycle in response to the average reference value being greater than the average value; and
further comprising:
comparing the drive signal to a maximum drive signal; and
triggering an alert in response to the drive signal being greater than the maximum drive signal.

Item 23. The method of any of items 16 through 22, wherein each device operated in emitting mode during the cycle contributes to the detection output, and further comprising determining a variability of each device operating in detecting mode during the cycle using a detection output contributed by the device when the device operates in detecting mode during the cycle; and generating a feedback signal that changes an intensity of radiation emitted by at least one of the devices operating in emitting mode during a subsequent cycle in response to the variability of at least one of the devices being below a variability reference value.

Item 24. The method of item 23, further comprising monitoring at least one device of the multiple devices for changes in variability in response to a variability of the device being above the variability reference value.

Item 25. A system comprising:

multiple devices configured to operate in emitting mode and detecting mode, each of the devices configured to emit and detect radiation that is germicidal in wavelength and intensity;

at least one drive source, each of the multiple devices configured to operate in emitting mode when connected to the drive source in a forward bias configuration and to operate in detecting mode when disconnected from the drive source or when connected to the drive source in a reverse bias configuration;

switching circuitry coupled to each of the multiple devices and to the drive source;

cycling circuitry configured to generate a sequence of control signals that control the switching circuitry to change the connections of the devices to the drive source in a cycle in which one or more of the multiple devices is switched to detecting mode and senses radiation emitted by one or more of the multiple devices simultaneously operating in emitting mode, each device operating in detecting mode generating a signal in response to the sensed radiation;

detection circuitry configured to detect signals of the devices operating in detecting mode and to generate a detection output in response to the detected signals; and monitoring/control circuitry configured to monitor the detection output for a low radiation intensity condition, the cycling circuitry and the monitoring/control circuitry implemented as a microprocessor executing programmed instructions.

Various modifications and alterations of the embodiments discussed above will be apparent to those skilled in the art, and it should be understood that this disclosure is not limited to the illustrative embodiments set forth herein. The reader should assume that features of one disclosed embodiment can also be applied to all other disclosed embodiments unless otherwise indicated.

The invention claimed is:

1. A system comprising:
multiple devices configured to operate in emitting mode and detecting mode, each of the multiple devices configured to emit and detect radiation that is germicidal in wavelength and intensity;
at least one drive source, each of the multiple devices configured to operate in emitting mode when connected to the at least one drive source in a forward bias configuration and to operate in detecting mode when disconnected from the at least one drive source or when connected to the at least one drive source in a reverse bias configuration;
switching circuitry coupled to each of the multiple devices and to the at least one drive source;
cycling circuitry configured to generate a sequence of control signals that control the switching circuitry to change the connections of the multiple devices to the at least one drive source in a cycle in which one or more of the multiple devices is switched to detecting mode and senses radiation emitted by one or more of the multiple devices simultaneously operating in emitting mode, each of the one or more of the multiple devices operating in detecting mode generating a signal in response to the sensed radiation;
detection circuitry configured to detect signals of the each of the one or more of the multiple devices operating in detecting mode and to generate a detection output in response to the detected signals; and
monitoring/control circuitry configured to monitor the detection output for a low radiation intensity condition.

2. A system comprising:
multiple devices configured to operate in radiation emitting mode and radiation detecting mode, each of the multiple devices configured to emit and detect radiation that is germicidal in wavelength and intensity;
at least one drive source, each of the multiple devices configured to operate in emitting mode when connected to the at least one drive source in a forward bias configuration and to operate in detecting mode when disconnected from the at least one drive source or when connected to the at least one drive source in a reverse bias configuration;
switching circuitry coupled to each of the multiple devices and to the at least one drive source;
cycling circuitry configured to generate a sequence of control signals that control the switching circuitry to change the connections of the multiple devices to the at least one drive source in a cycle in which one or more of the multiple devices is switched to detecting mode and senses radiation emitted by one or more of the multiple devices simultaneously operating in emitting mode, each of the one or more of the multiple devices operating in detecting mode generating a signal in response to the sensed radiation; and
detection circuitry configured to detect signals of the each of the one or more of the multiple devices operating in detecting mode and to generate a detection output in response to the detected signals; and
wherein
each of the one or more of the multiple devices when operated in emitting mode during the cycle contributes to the detection output; and
a monitoring/control circuitry is configured to:
determine an average value of the detection output;
compare the average value to an average reference value; and
generate a feedback signal that changes a drive signal of the at least one drive source during a subsequent cycle in response to the average reference value being different from the average value.

3. The system of claim 2, wherein the cycling circuitry is configured to switch each of the multiple devices to operate in detecting mode at least once during the cycle.

4. The system of claim 2, wherein the cycling circuitry is configured to switch some but not all of the multiple devices to operate in detecting mode during the cycle.

5. The system of claim 2, wherein the cycling circuitry is configured to switch the multiple devices one-by-one to operate in detecting mode during the cycle.

6. The system of claim 2, wherein, during each cycle, each of the one or more of the multiple devices operating in detecting mode is arranged to sense radiation emitted by two of the one or more of the multiple devices operating in emitting mode.

7. The system of claim 2, wherein a period of time that the one or more of the multiple devices operate in detecting mode during the cycle vary.

8. The system of claim 2, wherein:
the cycling circuitry comprises a microcontroller executing programmed instructions; and
the detection circuitry comprises a trans-impedance amplifier.

9. The system of claim 2, wherein the monitoring/control circuitry is configured to compare the detection output to a predetermined threshold and to generate an alert in response to the detection output being below the predetermined threshold.

10. The system of claim 2, wherein the monitoring/control circuitry is configured to:
compare the drive signal to a maximum drive signal; and
trigger an alert in response to the drive signal being greater than the maximum drive signal.

11. The system of claim 10, wherein the monitoring/control circuitry is configured to:
compare a detection output contributed by each of the multiple devices to a reference value of each of the multiple devices; and
generate a feedback signal that changes the drive signal of the at least one drive source in response to the detection output contributed by at least one of the multiple devices being different from the reference value of the at least one of the multiple devices.

12. The system of claim 2, wherein each of the one or more of the multiple devices operated in emitting mode during the cycle contributes to the detection output; and
the monitoring/control circuitry is configured to:
determine a variability of each of the one or more of the multiple devices operating in detecting mode during the cycle using the detection output contributed by the each of the one or more of the multiple devices; and
generate a feedback signal that changes a drive signal of the at least one drive source during a subsequent cycle in response to the variability of at least one of the multiple devices being below a variability reference value.

13. The system of claim 12, wherein the monitoring/control circuitry is configured to monitor each of the one or more of the multiple devices for changes in the variability in response to the variability of one or more of the multiple devices being above the variability reference value.

14. The system of claim 2, wherein the multiple devices are arranged so that the radiation emitted by at least one of the multiple devices operating in emitting mode is reflected from one or more surfaces towards the at least one device operating in detecting mode.

15. The system of claim 2, wherein the multiple devices are arranged so that at least one of the multiple devices operating in detecting mode detects the radiation emitted by at least one of the multiple devices operating in emitting mode, wherein the radiation is transmitted through one or more containers configured to contain a fluid.

16. A method comprising:
operating multiple devices configured to emitting and detecting radiation that is germicidal in wavelength and intensity in a cycle by generating a sequence of control signals that switch one or more of the multiple devices to detecting mode during the cycle;
each device of the multiple devices, when operating in detecting mode, sensing radiation emitted by one or more of the multiple devices simultaneously operating in emitting mode and generating an electrical signal responsive to the sensed radiation; and
detecting electrical signals of the each device of the multiple devices operating in detecting mode and generating a detection output in response to the detected electrical signals, the detection output indicating an intensity of the radiation sensed by the each device of the multiple devices operating in detecting mode during the cycle; and
wherein each of the one or more of the multiple devices when operated in emitting mode during the cycle contributes to the detection output, and further comprising:
determining an average value of the detection output;
comparing the average value to an average reference value; and
generating a feedback signal that increases or decreases an intensity of radiation emitted by the one or more of the multiple devices operating in emitting mode during a subsequent cycle in response to the average reference value being different from the average value.

17. The method of claim 16, wherein operating the multiple devices comprises switching each device of the multiple devices to detecting mode at least once during the cycle.

18. The method of claim 16, wherein operating the multiple devices comprises switching some but not all of the multiple devices to operate in detecting mode at least once during the cycle.

19. The method claim 16, wherein operating the multiple devices comprises switching the multiple devices one-by-one to operate in detecting mode during the cycle.

20. The method of claim 16, further comprising:
comparing the detection output to a predetermined threshold; and
generating an alert in response to the detection output being below the predetermined threshold.

21. The method of claim 16, wherein:
the feedback signal changes a drive signal of a drive source during a subsequent cycle in response to the average reference value being greater than the average value; and
further comprising:
comparing the drive signal to a maximum drive signal; and
triggering an alert in response to the drive signal being greater than the maximum drive signal.

22. The method of claim 16, wherein each of the one or more of the multiple devices operated in emitting mode during the cycle contributes to the detection output, and further comprising:
determining a variability of each of the one or more of the multiple devices operating in detecting mode during the cycle using a detection output contributed by each of the one or more of the multiple devices operating in detecting mode during the cycle; and
generating a feedback signal that changes an intensity of radiation emitted by at least one of the one or more of the multiple devices operating in emitting mode during a subsequent cycle in response to the variability of the at least one of the one or more of the multiple devices being below a variability reference value.

23. The method of claim 22, further comprising monitoring at least one device of the multiple devices for changes in variability in response to a variability of the at least one device being above the variability reference value.

\* \* \* \* \*